US008268551B2

(12) United States Patent
Tong

(10) Patent No.: US 8,268,551 B2
(45) Date of Patent: Sep. 18, 2012

(54) SENSITIVE SENSING BASED ON OPTICAL NONLINEAR WAVE MIXING

(75) Inventor: William G. Tong, La Jolla, CA (US)

(73) Assignee: San Diego State University Foundation, San Diego, CA (US)

( * ) Notice: Subject to any disclaimer, the term of this patent is extended or adjusted under 35 U.S.C. 154(b) by 0 days.

(21) Appl. No.: 10/540,224

(22) PCT Filed: Jan. 27, 2004

(86) PCT No.: PCT/US2004/002409
§ 371 (c)(1),
(2), (4) Date: Aug. 8, 2006

(87) PCT Pub. No.: WO2004/068087
PCT Pub. Date: Aug. 12, 2004

(65) Prior Publication Data
US 2006/0263777 A1    Nov. 23, 2006

Related U.S. Application Data

(60) Provisional application No. 60/443,225, filed on Jan. 27, 2003.

(51) Int. Cl.
*C12Q 1/68* (2006.01)
(52) U.S. Cl. ..................................... 435/6.1
(58) Field of Classification Search .............. 435/6
See application file for complete search history.

(56) References Cited

U.S. PATENT DOCUMENTS

| | | | |
|---|---|---|---|
| 4,284,354 A | 8/1981 | Liao | |
| 4,355,897 A | 10/1982 | Kaye | |
| 4,540,283 A | 9/1985 | Bachalo | |
| 4,622,642 A | 11/1986 | Bajard et al. | |
| 4,854,705 A | 8/1989 | Bachalo | |
| 5,166,507 A | 11/1992 | Davis et al. | |
| 5,600,444 A * | 2/1997 | Tong | 356/432 |
| 6,141,094 A | 10/2000 | Tong | |
| 6,248,540 B1 * | 6/2001 | Weinberg et al. | 435/7.1 |
| 2001/0033375 A1 * | 10/2001 | McFarland et al. | 356/364 |
| 2002/0015150 A1 * | 2/2002 | Armstrong et al. | 356/301 |
| 2003/0174324 A1 * | 9/2003 | Sandstrom | 356/317 |

OTHER PUBLICATIONS

Andrews, J., et al., "Atomic flame spectrometry based on polarization-modulated optical phase conjugation by resonant degenerate four-wave mixing", *Spectrochimica Acta Part B: Atomic Spectroscopy*, 44B(1):101-107, (1989).
Andrews, J., et al., "Doppler-Free Spectrum of the Barium $^1S_0$-$^1P_1$ Transition by Degenerate Four-Wave Mixing Using an Air/Acetylene Flame", *Applied Spectroscopy*, 45(4):697-700, (1991).
Atherton, A., et al., "Ultrasensitive absorption detection of protein and DNA microarrays based on nonlinear multi-photon wave-mixing spectroscopy", *Proc. SPIE*, vol. 5969, pp. 59690P, Sep. 2005.
Bao, X., et al., "Excited-state optical storage study in a dye-doped film using four-wave mixing spectroscopy", *Proc. SPIE*, vol. 2998, pp. 343-347, Jan. 1997.
Bao, X., et al., "Optical Nonlinearity and Multiplex Holographic Storage in Azo Side-Chain Liquid Crystalline Polymer", *Proc. SPIE*, vol. 3474, pp. 183-189, Oct. 1998.
Berniolles, S., et al., "Diode laser-based nonlinear degenerate four-wave mixing analytical spectrometry", *Spectrochimica Acta Part B: Atomic Spectroscopy*, 49B(12-14):1473-1481, Oct.-Dec. 1994.
Berniolles, S., et al., "Low-power compact laser-based nonlinear degenerate four-wave mixing detection for flowing liquids", *Proc. SPIE*, vol. 2546, pp. 145-151, Sep. 1995.
Berniolles, S., et al., "Sensitive absorbance measurement for gas-phase analytes based on multi-wave mixing spectroscopy", *Proc. SPIE*, vol. 2835, pp. 248-254, Nov. 1996.
Berniolles, S., et al., "Sensitive Capillary-Based On-Column Detection Method by Laser Wave Mixing", *Proc. SPIE*, vol. 2980, pp. 127-132, May 1997.
Berniolles, S., et al., "Sensitive On-Column Absorbance Detection of Native Molecules", *Proc. SPIE*, vol. 3270, pp. 200-206, May 1998.
Briggs, R., et al., "Sub-Doppler high-resolution wave-mixing detection method for isotopes in environmental applications", *Proc. SPIE*, vol. 5586, pp. 54-59, Dec. 2004.
Chen, D., et al., "High-resolution Laser Spectroscopy Based on Polarisation-modulated Optical Phase Conjugation in a Demountable Cathode Discharge", *J. Anal. Atomic Spectrometry*, vol. 3, pp. 531-535, Jun. 1988.
Kan, H., et al., "Sensitive wave-mixing detectors for capillary electrophoresis and liquid chromatography", *Proc. SPIE*, vol. 2835, pp. 135-142, Nov. 1996.
Knittle, J., et al., "Sensitive detection of enzyme activity by multi-photon nonlinear laser spectroscopy", *Proc. SPIE*, vol. 5587, pp. 177-182, Nov. 2004.
Lopez, M., et al., "Laser wave-mixing optical method for sensitive detection of analytes in microarrays and microchips", *Proc. SPIE*, vol. 5591, pp. 185-189, Dec. 2004.
Luena, G., et al., "Doppler-Free Laser Polarization Spectroscopy Using a Demountable DC Cathode Discharge Cell as a Trace Concentration Atomizer", *Applied-Spectroscopy*, 44(10):1668-1672, (1990).
Lyons, W., et al., "Nonlinear wave-mixing spectroscopy for sub-Doppler isotope analysis with trace-level detection sensitivity", *Proc. SPIE*, vol. 5971, pp. 597109, Sep. 2005.
Maniaci, M., et al., "Multiphoton laser wave-mixing absorption spectroscopy for samarium using a graphite furnace atomizer", *Spectrochimica Acta Part B: Atomic Spectroscopy*, 59(7):967-973, Jul. 2004.
Mann, B., et al., "Detection and imaging of nitrogen dioxide with the degenerate four-wave-mixing and laser-induced-fluorescence techniques", *Applied Optics*, 35(3):475-481, Jan. 1996.
Mickadeit, F., et al., "Sensitive Sub-Doppler Nonlinear Spectroscopy for Hyperfine Structure Analysis Using Simple Atomizers", *Proc. SPIE*, vol. 3270, pp. 168-173, May 1998.

(Continued)

*Primary Examiner* — Gary Benzion
*Assistant Examiner* — Cynthia Wilder
(74) *Attorney, Agent, or Firm* — Perkins Coie LLP

(57) ABSTRACT

Techniques and systems for using nonlinear four wave mixing to optically measure microarrays with sample cells of biological or chemical materials. Examples of suitable microarrays include but are not limited to DNA microchips and capillary electrophoresis microarrays.

12 Claims, 7 Drawing Sheets

OTHER PUBLICATIONS

Mickadeit, F., et al., "Sub-Parts-Per-Quadrillion-Level Graphite Furnace Atomic Absorption Spectrophotometry Based on Laser Wave Mixing", *Anal. Chem.*, 76(6):1788-1792, Mar. 2004.

Neyer, D.W., et al., "Circular Dichroism Spectroscopy Using Coherent Laser-Induced Thermal Gratings", *J. American Chemical Society*, 119(35):8293-8300, (1997).

Nunes, J., et al., "Circular Dichroism Spectroscopy by Four-Wave Mixing Using Polarization Grating-Induced Thermal Gratings", *J. Phys. Chem. A*, 101(18):3279-3283, (1997).

Nunes, J., et al., "Optical Fiber-Based Wave Mixing as a Convenient and Sensitive Laser Analytical Tool for Condensed-Phase Analytes", *Applied Spectroscopy*, 52(5):763-769, (1998).

Nunes, J., et al., "Optical Fiber-Based Wave-Mixing Probe", *Proc. SPIE*, vol. 2980, pp. 429-433, May 1997.

Nunes, J., et al., "Sensitive Circular Dichroism Spectroscopy Based on Nonlinear Degenerate Four-Wave Mixing", *Anal. Chem.*, 65(21):2990-2994, Nov. 1993.

Nunes, J., et al., "Sensitive laser wave-mixing detection methods for biomedical applications", *Proc. SPIE*, vol. 2388, pp. 205-212, May 1995.

Tong, W., et al., "Doppler-Free Spectroscopy Based on Phase Conjugation by Degenerate Four-Wave Mixing in Hollow Cathode Discharge", *Applied Spectroscopy*, 41(4):586-590, (1987).

Tong, W., et al., "Laser Spectrometry Based on Phase Conjugation by Resonant Degenerate Four-Wave Mixing in an Analytical Flame", *Anal. Chem.*, 59(6):896-899, Mar. 1987.

Weed, K., et al., "Sensitive sub-Doppler multiwave-mixing spectroscopy for flame and graphite furnace atomizers", *Proc. SPIE*, vol. 2385, pp. 157-164, Apr. 1995.

Weed, K., et al., "Trace Analysis of Rubidium Hyperfine Structure in a Flame Atomizer Using Sub-Doppler Laser Wave-Mixing Spectroscopy", *Applied Spectroscopy*, 57(12):1455-1460, Dec. 2003.

Wu, Z., et al., "Absorbance detection of amino acids by laser wave mixing in microbore liquid chromatography", *J. of Chromatography A*, 805(1-2):63-69, May 1998.

Wu, Z., et al., "Doppler-free measurement of the calcium $4s^2\ ^1S_0$-$4s4p\ ^1P_1$ transition at 422.673 nm by degenerate four-wave mixing in a demountable cathode discharge atomizer", *Spectrochimica Acta Part B: Atomic Spectroscopy*, 47B(3):449-457, Mar. 1992.

Wu, Z., et al., "Forward-Scattering Degenerate Four-Wave Mixing as a Simple Sub-Attomole-Sensitive Nonlinear Laser Analytical Spectrometric Method", *Anal. Chem.*, 65(2):112-117, Jan. 1993.

Wu, Z., et al., "Laser Analytical Spectrometry Based on Optical Phase Conjugation by Degenerate Four-Wave Mixing in a Flowing Liquid Analyte Cell", *Anal. Chem.*, 61(9):998-1001, May 1989.

Wu, Z., et al., "Sensitive absorbance detection method for capillary electrophoresis based on laser wave-mixing", *J. of Chromatography A*, vol. 773, pp. 291-298, (1997).

Wu, Z., et al., "Sensitive absorbance measurement method based on laser multi-wave mixing", *Spectrochimica Acta Part B: Atomic Spectroscopy*, 49B(12-14):1483-1489, Oct.-Dec. 1994.

Wu, Z., et al., "Stable Isotope Ratio Analysis at Trace Concentrations Using Degenerate Four-Wave Mixing with a Circularly Polarized Pulsed Probe Beam", *Anal. Chem.*, 63(9):899-903, May 1991.

Wu, Z., et al., "Trace-Concentration Detection of Cobalt in a Liquid Flow Cell by Degenerate Four-Wave Mixing Using Low-Power Off-Resonant Laser Excitation", *Anal. Chem.*, 63(18):1943-1947, Sep. 1991.

\* cited by examiner

SENSITIVE SENSING BASED ON OPTICAL NONLINEAR WAVE MIXING

This application is a national stage application of and claims the benefit of PCT/US2004/002409 filed on Jan. 27, 2004, which claims the benefit of U.S. Provisional Application No. 60/443,225 entitled "SENSITIVE SENSING BASED ON OPTICAL NONLINEAR WAVE MIXING" and filed on Jan. 27, 2003 by William G. Tong. Both applications are incorporated herein by reference in their entirety.

BACKGROUND

This application relates to optical sensing of various materials, including chemical and biological substances.

Nonlinear four wave mixing is an optical process in an optical medium where three coherent optical waves interact with one another through nonlinear coupling to produce a fourth coherent signal wave. The nonlinearities of the medium, primarily the third-order nonlinear susceptibility of the medium in some implementations, contribute to such nonlinear coupling. The signal wave includes information on optically-excited atoms or molecules present in the medium where the three input optical waves intersect and hence can be collected to extract information about the medium. The strength of the signal wave is associated with the population of atoms or molecules and the spectral characteristics of the signal wave can be analyzed to reveal the structure of the atoms or molecules of interest. The coherent characteristics of the four-wave mixing signal beam have a number of advantages, including a laser-like signal beam, efficient signal collection, excellent spatial resolution, and sub-Doppler spectral resolution. Hence, four-wave mixing has been widely used as a highly sensitive tool in spectroscopic measurements.

Various four wave mixing systems may be used for detection of a minute amount of a substance. For example, U.S. Pat. No. 5,600,444 to Tong describes devices and techniques for using two-input-beam forward-scattering degenerate four-wave mixing to achieve ultrasensative analytical measurements of an analyte. Backward-scattering degenerate four-wave mixing has also be used for sensitive laser spectroscopic detection. See, e.g., U.S. Pat. No. 6,141,094 to Tong.

SUMMARY

This application includes techniques for using four wave mixing in microarrays with sample cells of biological or chemical materials. Examples of suitable microarrays include but are not limited to DNA microchips and capillary electrophoresis microarrays.

In one implementation, a microarray is provided to include DNA cells. The microarray is placed in an optical degenerate four-wave mixing (DFWM) system operating at an optical wavelength within an absorption spectral range of the DNA cells to generate a DFWM signal in one DNA cell. The DFWM signal is collected and measured. Next, the mciroarray is scanned in position to place other DNA cells in the DFWM system to get respective DFWM signals.

In another implementation, a microchip is provided to include metal ions chelated in a compound in a solution. A capillary electrophoresis process is performed to separate the metal ions from the compound in the solution. Optical beams are directed to overlap on the microchip in a four wave mixing configuration to obtain a wave mixing signal. The wave mixing signal is then used to determine a concentration of the metal ions.

Laser wave mixing systems are also described in this application. In one implementation, a system includes a laser to produce a laser beam, means for splitting the laser beam into a pump beam and a probe beam, means for directing the pump and probe beams to overlap at a sample location in a forward-scattering four wave mixing configuration, a microarray having cells located to place one cell in the generate a wave mixing signal, and an optical detector located to receive the wave mixing signal.

In the above and other implementations, forward-scattering four wave mixing configurations may be used. Backward-scattering four wave mixing configurations may also be used.

These and other implementations and their variations are now described in greater detail in the following drawings, detailed description, and the claims.

DETAILED DESCRIPTION

Figure 1A:
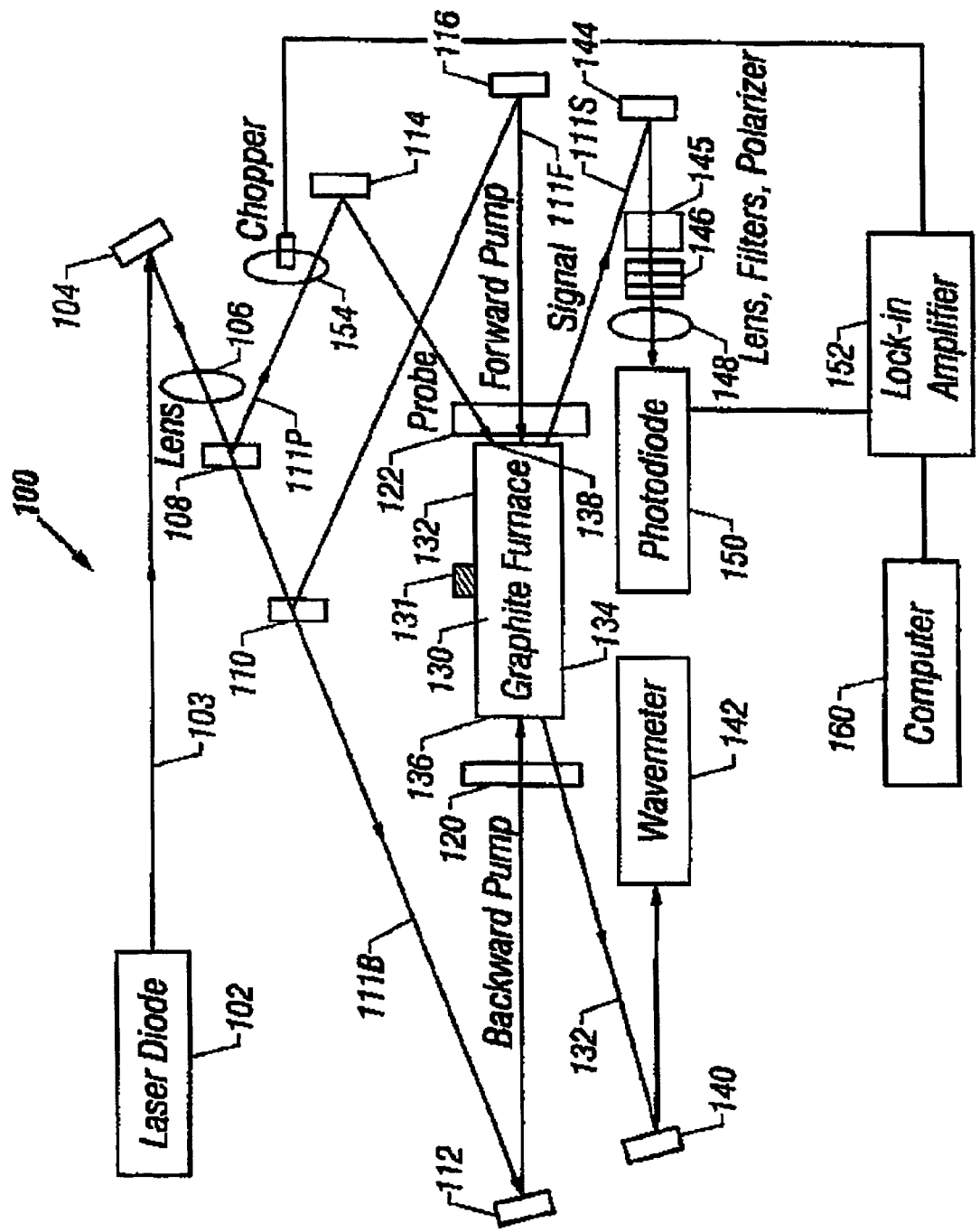
FIG. 1a schematically shows one example 100 of a four-wave-mixing spectroscopic analyzer in a backward-scattering degenerate four wave mixing configuration.

Optical sensing devices and techniques of this application are designed for highly sensitive, selective and high-resolution sensing of various materials based on nonlinear laser wave mixing. Such sensing devices may be implemented using, among others, microfluidic devices, laboratory-on-a-chip, fiber optics, and capillary cells for potential chemical, biological and environmental applications. Exemplary implementations of nonlinear wave mixing for measurements in microarrays are described.

Nonlinear optical wave mixing may be implemented in optical sensing systems with different configurations. Examples of such configurations may be found in U.S. Pat. No. 5,600,444 issued Feb. 4, 1997 and U.S. Pat. No. 6,141,094 issued Oct. 31, 2000, the entire disclosures of which are incorporated herein by reference as part of the specification of this application. Techniques and features in the above-referenced patents may be used or combined with the techniques described in this application. Notably, the nonlinear multi-photon laser wave-mixing optical methods may be implemented in portable, robust and compact systems for a wide range of applications, including, but not limited to, biomedical applications. Advantages of such techniques and systems include high spatial resolution and sensitivity, versatile applications, ease of operations, convenient procedures, and less tedious chemical steps, etc. Taking advantage of small probe volumes available, this method can be easily interfaced and adapted to small, relatively portable, robust, microfluidic devices.

As an example, the nonlinear wave mixing techniques for sensitive high-resolution detection may be implemented with high temperature atomizers including graphite discharge plasmas, graphite furnace, inductively coupled plasma, and flame atomizers with detection sensitivity levels in the sub-parts-per-quadrillion levels. Applications to liquid-phase samples can achieve high detection sensitivity levels.

The laser wave mixing methods offer many potential applications in many fields including chemistry, biology, and medicine. For example in biotechnology, laser wave mixing could be used for detecting biomolecules (e.g., proteins, DNAs, etc.) with or without labels or tags, for studying enzyme activities, for monitoring smaller chemical/biological changes more dramatically with less tedious procedures, for studying bio molecular structures, for analysis of small bio cells with high spatial resolution, for sensitive detection as sensors, and many other potential applications.

The laser wave mixing based detection methods may be useful for various applications in a wide range of fields for measuring atoms, isotopes (gas-phase) and molecules (liquid-phase) at detection levels that may be difficult to achieve with other sensing techniques. For example, laser wave mixing may be used to improve the detection sensitivity by a factor of about 1,000 to 1,000,000 relative to other sensing techniques. For example, preliminary detection limits for laser wave mixing may be obtained at sub-parts-per-quadrillion level, sub-attogram, sub-zeptomole, and sub-femto molar detection limits. Laser wave mixing may be effectively interfaced to popular gas-phase atomizers and liquid-phase flow systems for highly sensitive detection of e.g., gas-phase atoms and isotopes, at sub-Doppler spectral resolution and sensitive detection of liquid samples.

Laser wave mixing can produce positive signals against dark background for easy detection with a high sensitivity. Nanoliter- and picoliter-level probe volumes and spatial resolution can be achieved. Efficient use of short absorption path lengths can be achieved in laser wave mixing in various configurations, including simple two-input-beam planar (2-D) and three-input-beam non-planar (3-D) optical configurations. As described below, aperture templates may be implemented in laser wave mixing for effective and reliable optical alignment. Laser wave mixing allows for relatively low operating laser power, e.g., milliwatts for CW lasers, and nanojoules for pulsed lasers. Hence, low-power, compact, and inexpensive solid-state lasers may be used. The nature of the laser wave mixing allows for effective use of polarization, wavelength and other modulation methods to enhance the measurement sensitivity. Optical phase conjugation may be used in the laser wave mixing to achieve unique optical measurement advantages not readily available in other optical methods. Laser wave mixing may be applicable to fluorescing, weakly fluorescing, and non-fluorescing samples.

Under proper designs, laser wave mixing may be easily interfaced with a wide range of chemical instruments. Examples of the instruments include but are not limited to gas chromatographs (GC), liquid chromatographs (LC), mass spectrometers (MS), GC-MS, LC-MS, inductively coupled plasmas (ICP), ICP-MS, high performance/power capillary electrophoresis (HPCE) systems, flow injection analysis (FIA) systems.

FIG. 1a schematically shows one embodiment 100 of a four-wave-mixing gas-phase spectroscopic analyzer in a backward-scattering degenerate four wave mixing configuration where three input beams, i.e., a forward pump, a backward pump, and a probe, are coupled into the sample under measurement. A laser 102, e.g., a diode laser, produces a tunable coherent beam 103. The laser 102 is tuned to a desired wavelength with a selected spectral line of a sample under measurement. A mirror 104 and a lens 106 guide the beam 103 to beam splitters 108 and 110. The beam splitter 108 reflects a portion of the beam 103 as a probe beam 111P and transmits the remaining part of the beam 103 to the beam splitter 110. The beam splitter 110 produces a forward pump beam 111F by reflection and a backward pump beam 111B by transmission. Mirrors 112, 114, and 116 are positioned to respectively guide the backward pump beam 111B, the probe beam 111P, and the forward pump beam 111F so that they cross and overlap with one another. The probe beam 111P and the forward pump beam 111F cross each other to form an acute angle. A sample holder 130, such as a DNA microarray chip or a gas-phase atomizer (e.g., a graphite furnace electrothermal atomizer), is used to produce a sample in a location where the beams overlap. In the following description, an atomizer is used as an example for the sample holder 130 to produce a sample vapor under measurement. The sample holder 130 has a chamber with a top wall 132 and a bottom wall 134, and two side windows 136 and 138 for receiving optical signals. A sample is resolved in a solvent which is injected from an injection port 131 on the top wall 132 into the atomizer 130. The injected liquid drops to the bottom wall 134 and becomes vaporized. A computer 160 is included in the analyzer 100 to process and store signals from the photodetector 150. The computer 160 may also function as a system controller to control operations of the atomizer 130 or the laser 102.

The probe beam 111P, the forward pump beam 111F, and the backward pump beam 111B as shown form a three-dimensional, non-planar, four-wave-mixing configuration. The probe beam 111P is in a different plane than the plane defined by the pump beams 111F and 111B. When two input beams intersect at a small angle in an optical medium, constructive and destructive interferences of these beams form periodic modulation in the medium. Two of the three input beams write a grating inside the graphite furnace, and the third input beam scatters off the grating to produce the fourth coherent signal beam 111S. The difference between ground- and excited-state populations across the modulation or gratings depends on the excitation wavelength and the angle between the grating-writing beams. The signal beam 111S is generated in an optical path different from the probe beam 111P and can be directly collected by a photodetector 150 (e.g., a photodiode). A detection module 142 is also positioned relative to the furnace chamber 130 to receive the transmitted probe beam 132 and measures certain properties of the transmitted probe beam 132. For example, the detection module 142 may include a wavemeter to measure the wavelength of the probe beam for spectroscopic analysis.

Figure 1B:
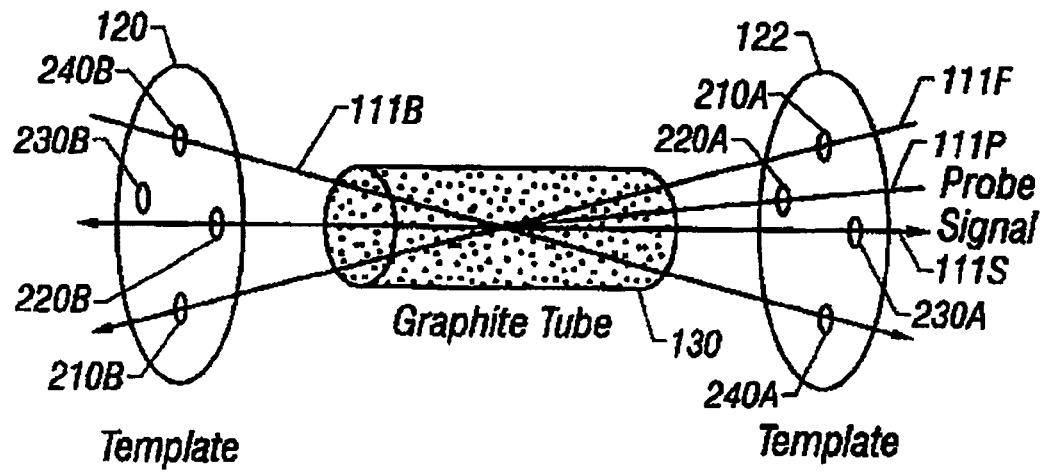
FIG. 1b shows one implementation of alignment templates for the system in FIG. 1a, where numerals used are applicable to FIGS. 1a and 1b only.

Two alignment templates 120 and 122 are respectively placed on two sides of the furnace chamber 130 for pre-alignment of the three input beams 111P, 111F, and 111B. FIG. 1b shows one exemplary implementation of the alignment templates 120 and 122. Each alignment template may be an opaque mask having at least three specially designed holes for transmitting beams. Thus, templates 120 and 122 also serve as spatial filters to prevent the scattered background light from reaching the detector 150. The templates 120 and 122 may be made by simply forming four small holes, one for each beam involved in a four-wave mixing process, in two thin aluminum plates. The pattern formed by the holes in one template is inversely symmetric with respect to the pattern formed by the holes in another template. In FIG. 1b, the templates 122 and 120 have holes 210A, 220A, 230A, 240A and 210B, 220B, 230B, 240B, respectively. The templates 122 and 120 are positioned relative to the furnace chamber 130 so that holes 210A and 210B define the path of the forward pump 111F, holes 220A and 220B define the path of the probe 111P, holes 230A and 230B define the path of the signal beam 111S, and holes 240A and 240B define the path of the backward pump 111B. The positions of holes 230A and 230B can be determined based on given directions of beams 111F, 111B, and 111P according to the vector conservation requirement of the four-wave mixing process. The pump beams 111F and 111B may be opposing each other, where the beam 111F goes through the holes 210A and 210B and the beam 110B goes through the holes 240B and 240A. When the beams 111F and 111B are counter propagating, they go through the same pair of holes.

The positions of the templates 120 and 122 are fixed relative to each other for a desired four-wave mixing configuration. The chamber of the gas-phase atomizer 130 may be adjusted to change its position relative to the templates 120 and 122 so the laser beams can cross and overlap in a desired position within the chamber. The relative position of a hole relative to other holes in each template is selected so that the four beams 111F, 111B, 111P, and 111S overlap in a common volume with desired crossing angles with respect to one another at a desired spacing between two templates 120 and 122. The common volume is positioned within the furnace chamber 130 at where the sample vapor is located. Preferably, the forward pump beam 111F and the probe beam 111P form an acute crossing angle of less than about 20 degrees, more preferably less than 10 degrees, and most preferably, less than 5 degrees. This crossing angle is important since it affects the sharpness of gratings formed in the sample, the grating periods, and the grating washout due to thermal motion. The dimension of the holes is selected to control the beam size and also determines the volume of the overlap region at a given crossing angle between the beams 111F and 111P. The volume of the beam overlap region is adjustable and is usually smaller than the volume of the sample vapor produced in the furnace 130 so that the entire beam overlap volume is within the vapor volume. The dimension of the holes may be further adjusted to filter out the background noise in the signal beam 111S to achieve a desired signal-to-noise ratio.

Once the templates 120 and 122 are placed at their desired positions at both ends of the furnace 130, the optical components then can be pre-aligned. For example, the pre-alignment can be accomplished by using a visible alignment laser beam to produce four alignment beams to respectively trace the paths of beams 111F, 111B, 111P, and 111S. Thus, the first and second alignment templates 120 and 122 can be aligned in their desired positions relative to the chamber 130. Other beam guiding elements and the elements in the path of the signal beam 111S (e.g., detector 150) can also be aligned. Upon completion of the pre-alignment, the actual pump beams 111F and 111B and the probe beam 111P can be generated to trace the alignment beams. Therefore, implementation of templates 120 and 122 significantly simplifies the otherwise time-consuming optical alignment and optical maintenance of the system. This is especially important when using atomizers that do not fire continuously, and hence, the signal 111S is not continuously present. Thus, the optical alignment in general cannot be performed conveniently by using the generated four-wave mixing signal 111S during the transient period when the sample vapor exists.

Referring back to FIG. 1a, the spectrometer 100 may also include a polarizer 145, an optical bandpass filter 146, and a lens 148 in the optical path of the signal beam 111S. These components and the photodetector 150 can be pre-aligned by using an alignment beam, preferably visible, to trace the path of the signal beam 111S. The optical filter 146 is configured to transmit light at the signal wavelength and block light at other wavelengths such as the white light emitted from the graphite furnace 130. The polarizer 145 is aligned to have its polarization substantially parallel to the signal polarization to provide polarization discrimination. The polarizer 145 may also be used to implement polarization modulated detection techniques to increase the signal-to-noise ratio in the signal detection. When all three input beams are vertically polarized, for example, the signal beam 111S is vertically polarized; when one of the three input beams 111F, 111B, and 111P is orthogonally polarized relative to the other two input beams, the signal beam 111S is orthogonally polarized. Polarization properties of laser wave mixing can be advantageously used for many important applications including sensitive circular dichroism spectroscopy. In addition, the polarizer 145 blocks randomly-polarized background light from reaching the detector 150.

The spectrometer 100 can be operated in either a continuous sampling mode or a pulsed sampling mode. In the continuous sampling mode, the laser 102 produces a continuous wave beam 103. Hence, the signal 111S is also continuous. A lock-in amplifier 152 and a chopper 154 can be used to modulate one of the input beams (e.g., the probe beam 111P) in order to increase the signal-to-noise ratio. When the laser 102 is a pulsed laser, analyzer 100 operates in the pulsed sampling mode and a "boxcar" averager may be used to replace the lock-in amplifier. In either mode of operation, the total intensity of the beams 111F, 111B, and 111P is preferably at or close to the saturation intensity of the sample to achieve an efficient four-wave mixing. The saturation intensity generally varies from one sample to another depending on properties of the excited atomic or molecular transition in the sample. When the total intensity is above the saturation intensity of a sample, the efficiency of the wave mixing decreases and other adverse effects arise, including power broadening of the spectral line that reduces the spectral resolution. In addition, the laser 102 may be configured to produce a narrow linewidth to achieve a high spectral resolution in the sub-Doppler range since the counter-propagating configuration of the pump beams 111F and 111B essentially eliminates Doppler broadening. Further, the frequency of the laser 102 may be stabilized to avoid mode hopping and to further improve the spectral resolution and the signal-to-noise ratio. Preferably, the linewidth of the laser 102 is stabilized at about a few MHZ (e.g., 1 MHz).

The four-wave-mixing signal in general has a cubic dependence on the input laser power. The signal strength, and hence, the detection sensitivity can be further enhanced by using higher input beam intensities up to about the saturation intensity. The four-wave-mixing signal also has a quadratic dependence on absorption coefficient. For analytes with low absorption coefficients, the wave-mixing detection sensitivity is still comparable to or better than those of conventional laser methods because of the nonlinear signal properties such as cubic power dependence, virtually 100% optical collection efficiency, and the laser-like coherence properties of the signal beam. For example, unlike laser-induced fluorescence methods where the signal is a small fraction of a widely diffused fluorescence signal laser, the wave-mixing signal is a collimated coherent laser-like beam and hence nearly the entire signal beam can be directed into a photodetector. Furthermore, since wave mixing is an absorption method, both fluorescing and non fluorescing analytes can be measured.

Figure 2A:
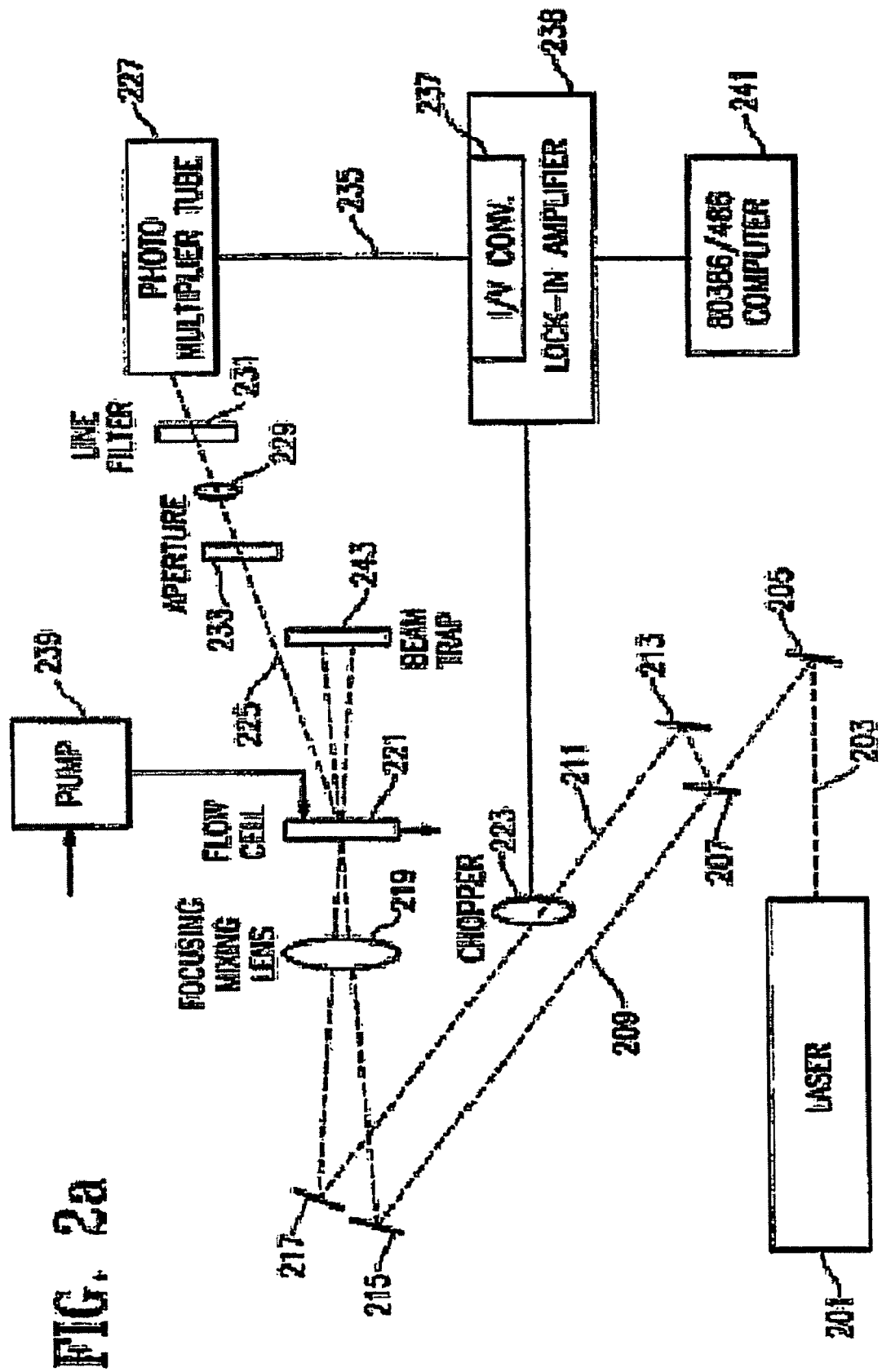
FIGS. 2a, 2b, 2c, and 2d show examples of forward D4WM systems for measuring various materials, where numerals are applicable only to FIGS. 2a through 2e.

FIG. 2a shows one example of a two-input-beam forward-scattering degenerate four-wave mixing F-D4WM arrangement. It should be understood that the particular arrangement of reflectors and beam splitters is provided only as an exemplar only. This system includes an excitation light source 201, which may be a compact diode laser, such as is commonly known. Alternatively, a helium-neon laser, a continuous-wave argon ion laser or a Nd:YAG laser may be used. A laser beam 203 output by the light source 201 is preferably reflected by a reflector 205 and split by a beam splitter 207 to form a first 209 and a second 211 input beam. The second input beam 211 is reflected by a second reflector 213 such that the first 209 and second 211 input beams are preferably generally parallel. The intensity 11, of the first input beam 209 with respect to the intensity 12 of the second input beam 211 arriving at the sample cell, 11:12, is approximately 7:3 to generate the signal in one direction only. The preferred ratio is 1:1 to generate two signal beams.

A third reflector 215 and a fourth reflector 217 redirect the first input beam 209 and the second input beam 211, respectively, toward a single 100-mm focusing lens 219. The focusing lens 219 preferably focuses and mixes both input beams 209, 211. A sample holder 221 is placed at the lens' focal point. The sample holder 221 may be a DNA microarray chip, a sample cell, or other devices holding the sample under measurement. The diameter of both the first input beam spot and the second input beam spot on the sample cell 221 may be approximately 34 micros as one example. The first input beam 209 and the second input beam 211 intersect inside the sample cell 221 with an intersect angle which may be approximately 1.5 degrees or less. The small input beam spots allow the system to interface directly with systems in which an analyte is available in a small volume, such as a cell in a microarray chip, the capillary tube of a high power/high performance capillary electrophoresis system (HPCE), the column of a high performance liquid chromatography (HPLC) system, or to directly probe a small volume inside a gas-phase atomizer such as flame, dc plasma, graphite furnace, inductively coupled plasma, with high spatial resolution in diagnostic studies.

In order to optimize the signal strength of a phase-conjugate signal which is generated, the difference in path lengths (or distances traveled) for first input beam 209 and the second input beam 211 are preferably kept to less than the coherence length of the laser. A device for amplitude modulating the second input beam 211, such as a mechanical light chopper 223 (for example, Model 03-OC4000, manufactured and distributed by Photon Technology International Inc., Princeton, N.J.), or any solid state electronic light intensity modulation device, is used. A phase-conjugate signal beam 225 generated in the sample cell 221 is directed to a detector 227, such as a photomultiplier tube (e.g., Model R928, manufactured and distributed by Hamamatsu Corp., Middlesex, N.J.) after passing through a lens 229 preferably having a 250-mm focal length and preferably a filter 231 which in the preferred embodiment is a 514.5 nm laser-line filter when using an argon ion laser. A small aperture 233 is preferably disposed in front of the detector 227 to minimize background noise due to the scattering of the two input beams 209 and 211.

The electrical output signal 235 of the detector 227 is then preferably coupled to a current-to-voltage converter 237, the output of which is preferably monitored by a lock-in amplifier (otherwise known as phase sensitive amplifier) 238 (such as Model 5207, manufactured and distributed by Princeton Applied Research, Princeton, N.J.). The output from the detector 227 may also be coupled to other processor components 241, such as a strip-chart recorder, personal computer including an analog to digital converter, or any other such processing device. Control of the present invention may be performed by the same computer used to control a HPCE, HPLC, or atomizer system with which the present invention is being used.

In implementations where the sample holder 221 is a cell, the sample cell 221 may be the capillary of an HPCE system, the column of an HPLC system, or a gas-phase atomizer system (e.g., flame, de plasma, ICP plasma, graphite furnace). However, a rectangular glass flow cell with approximately a 0.1-mm optical path length (such as a Type 48, manufactured and distributed by Starna Cells, Inc., Atascadero, Calif.) may be used to measure an analyte for other purposes. Naturally, the sample cell 221 may take any form which can hold a volume of analyte which is at least equal to the spot volume of the focused input beams 209, 211, and which allows the input beams 209, 211 to enter and the signal beam 225 to exit without excessive attenuation. Furthermore, the analyte in the sample cell 221 may be any substance in any phase (i.e., liquid, solid, or gaseous), such as eosin B dissolved in ethanol and iodine in carbon tetrachloride. The present system is capable of analyzing solids and gases, as well as liquids.

An analyte solution may be delivered to the sample cell 221 in accordance with the system with which the present invention is being used. For example, the analyte is delivered by electrophoresis in an HPCE system or a pump in a HPLC system. Alternatively, a pump, such as a peristaltic pump 239 may be used to deliver the analyte to the sample cell 221.

After the two input beams 209, 211 pass through the sample cell 221, they are blocked by a beam trap 243, and the signal beam 225 is easily separated and directed toward the detector 227. An analyte solution with a relatively high concentration may be used as an "alignment solution" to optimize the optical alignment. A micromolar-level solution can generate a strong signal that is visible to the naked eye, thus allowing simple alignment of the present invention. Signal optimization is performed simply by adjusting the mirrors and the lenses, and by carefully adjusting the position of the sample cell 221 so that the sample cell 221 is at the focal point of the wave-mixing lens, while observing the strength of the visible signal spot on a card (or on a photodetector for trace-concentration analytes). Of course, any other means for determining the maximum strength of the signal beam 225 while adjusting the alignment of the system would be equally acceptable. For example, a self-adjusting system using feedback from the lock-in amplifier 238 might be used to determine the optimum alignment of the system. Once the optical alignment is optimized, the alignment and the signal remain very stable and different analyte solutions could be flowed through and analyzed without any further adjustments.

Figure 2B:
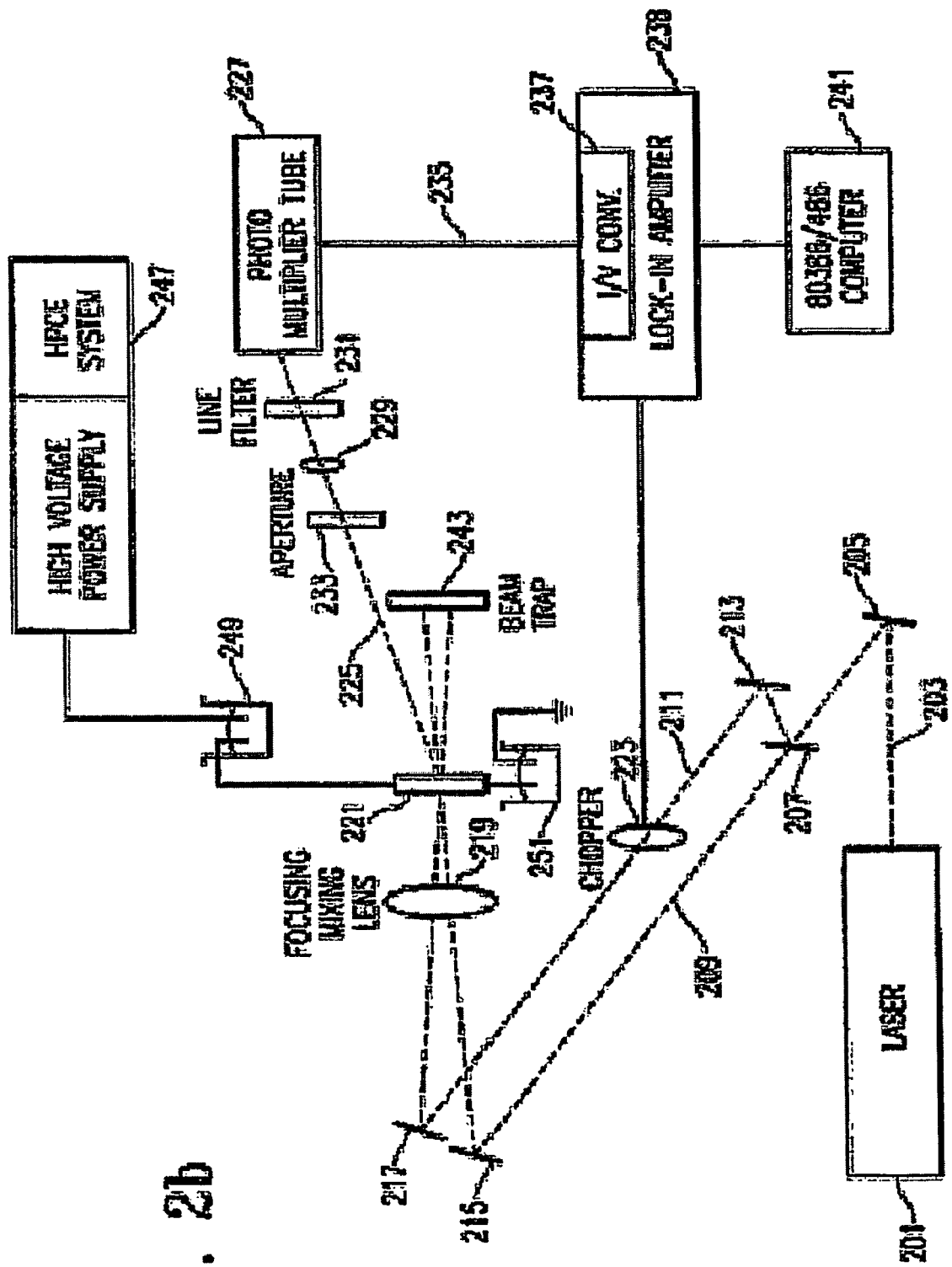

FIG. 2b illustrates an implementation two-input-beam wave mixing system coupled to the capillary tube of a HPCE system. The sample cell 221 is part of the capillary tube of the HPCE system. One end of the sample cell draws from a positive pool 249. The other end of the sample cell discharges into a negatively charged pool 251. A high voltage source is coupled to, and controlled by, the HPCE system controller 247.

Figure 2C:
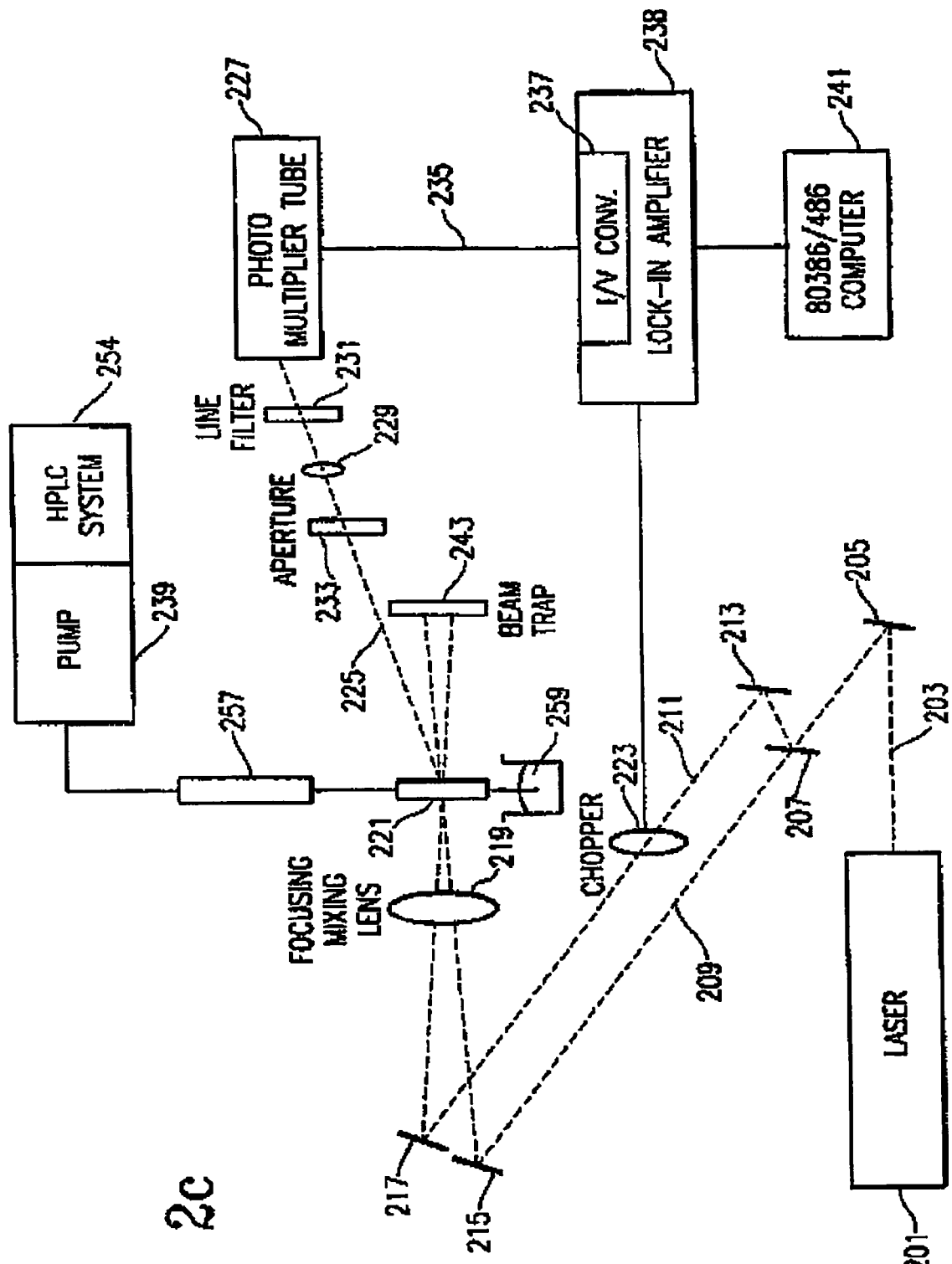

FIG. 2c illustrates another two-input-beam system coupled to a column 257 of a HPLC system. The sample cell 221 is coupled at one end to the column 257, and at the other end to a waste pool 259. A pump is coupled to, and controlled by, a HPLC system controller 255.

Figure 2D:
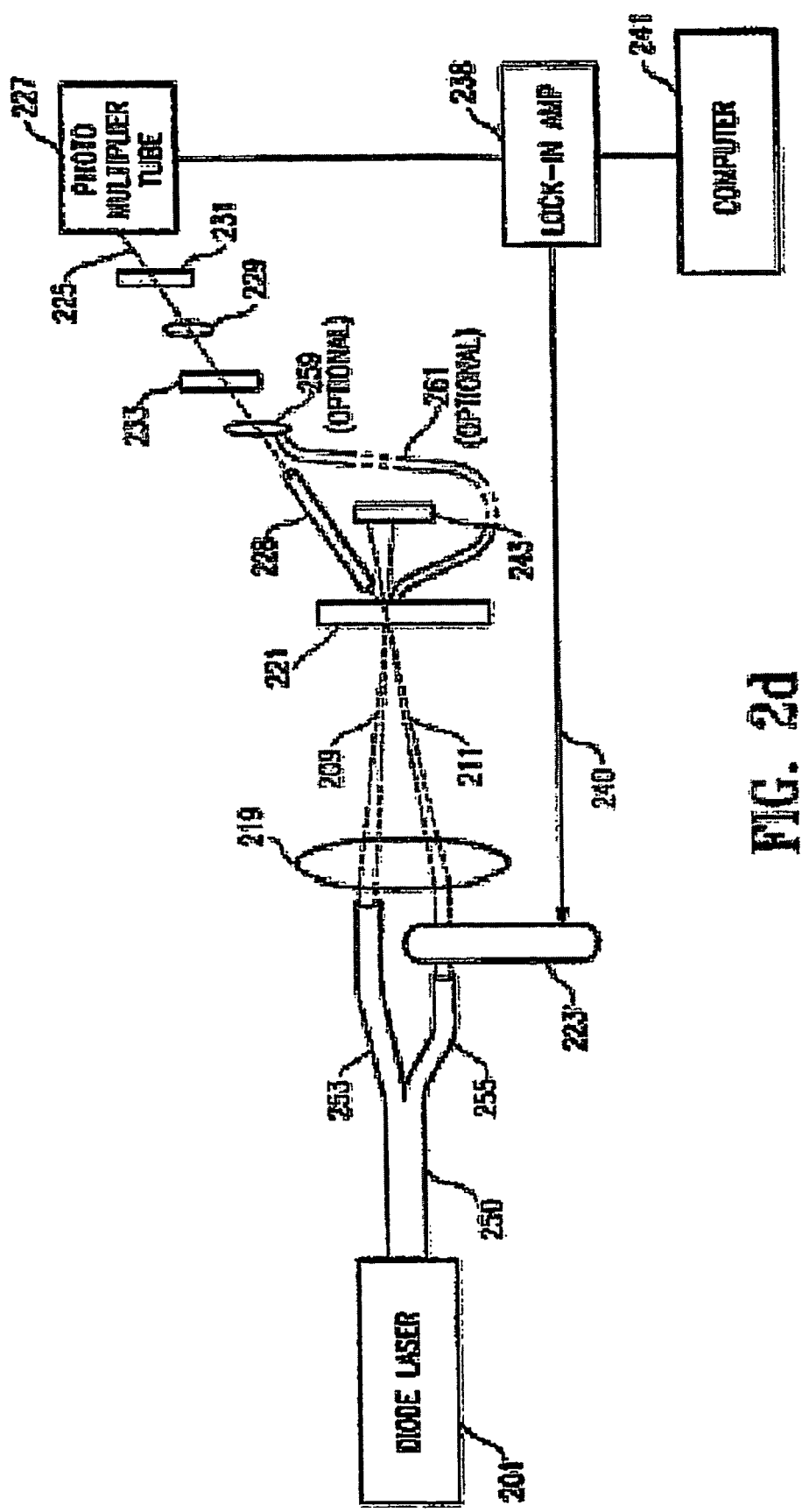

FIG. 2d further shows another example where the laser beams 209, 211, 225 are each transmitted through a fiber optic cable 250. Hence, transmission of laser light through air can be minimized. The fiber optic cable may be prealigned and bound to a substrate to prevent misalignment. The output of the laser source 201 may be coupled directly to the fiber optic cable 250 in known fashion. The fiber optic cable may be split into two sections 253, 255 in known fashion, thus dividing the beam into the first input beam 209 and the second input beam 211. The second section of fiber optic cable 255 may be coupled to an amplitude modulation device 2231, such as a well known mechanical chopper, or any solid state electronic light intensity modulation device or an electro-optical modulator. Use of an electronic circuit for modulating the second input beam 211 allows the system to be produced in a compact package. The output of the first section of fiber optic cable 253 and the output from the modulation circuit 223' are preferably coupled to a lens 219. The lens causes the two input beams 209, 211 to be focused to a fine point within a sample cell 221. The input beams 209, 211 are preferably trapped at the opposite side of sample cell 221 by a beam trap 243. A signal beam 225 is generated within the sample cell 221 and projects outward through an aperture 233, a lens 229, a line filter 231, and into a photomultiplier tube 227. The path from the sample cell 221 to the photomultiplier tube 227 may, be through a fiber optic cable 228. Alternatively, the path may be through air. In one alternative embodiment of the present invention, two signal beams 225, 303 may be coupled to the photomultiplier tube 227 through a summing lens 259 by fiber optic cable 261, or each signal beam 225 and 303 may be coupled to a separate photomultiplier or photodiode, via air or fiber optic cables and detected by summing or multiplication.

Figure 2E:
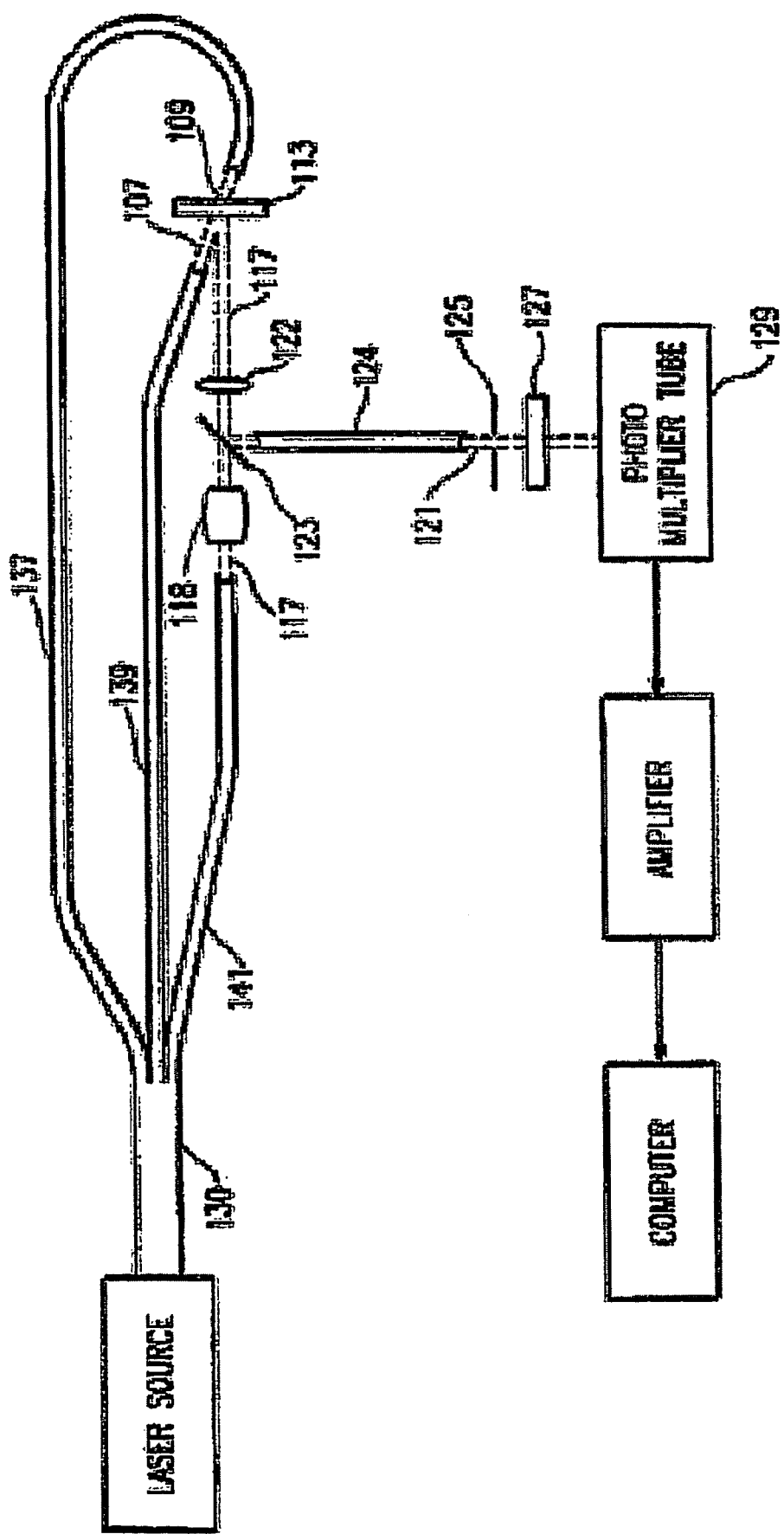
FIG. 2e shows an example of a backward D4WM system with fiber cables for routing beams.

FIG. 2e shows one backward D4WM system having fiber optic cable to minimize alignment difficulties. A fiber optic cable 130 is divided into three 137, 139, 141 such that the signal is split into three beams 107, 109, 117. One input beam 107 is preferably directed to the sample cell 113 at the appropriate angle by the fiber optic cable 139. The second input beam 117 is directed by the fiber optic cable 141 at a modulation device 118 and a beam splitter 123 which passes the entire input beam 117. The input beam 117 is focused by a lens 122. A signal beam 121 is generated within the sample cell 113 and transmitted along the path that the input beam 117 traverses from the beam splitter 123. Upon striking the beam splitter 123, the signal beam 121 is reflected toward an aperture 125. The signal beam 121 can be directed toward the photodetector via fiber optic cable or through air.

Figure 3:
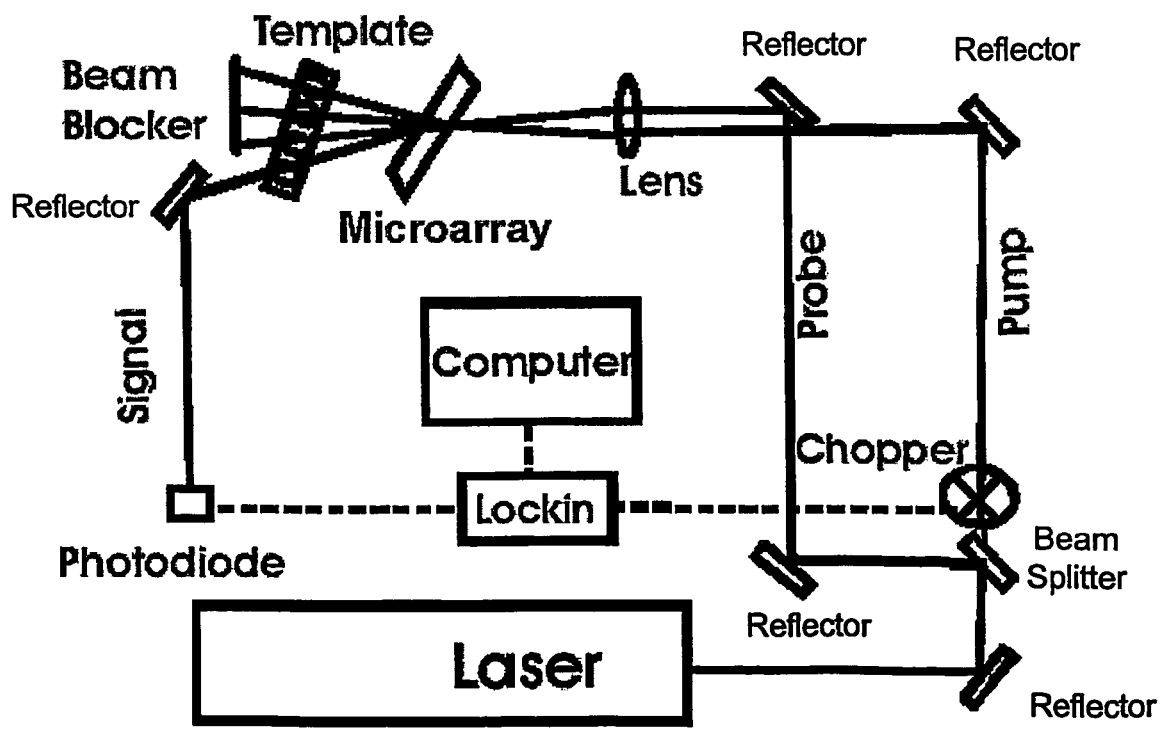
FIG. 3 shows an exemplary instrument that combines the D4WM with a microarray for detecting chemical or biological materials in the microarray cells.

FIG. 3 shows an exemplary instrument that combines a forward-scattering D4WM sensor with a microarray for detecting chemical or biological materials in the microarray cells. A laser such as an argon ion laser or other suitable laser with the desired laser wavelength is used to produce an input laser beam. The input beam is split into a pump beam and a probe beam via a beam splitter, e.g., with a ratio of 70:30. The pump and probe beams are then recombined and focused on the microarray slide (a microchip, a capillary channel, a waveguide, or a microfluidic device). A template with prearranged holes is placed at the back of the microarray to block all the other beams and only allow the signal beam to pass through to reach a photodetector which receives the signal beam. Other laser wave mixing systems such as the examples described above and others may also be used in combinations with microarray chips.

The combinations of microarray chips with D4WM sensors offer many potential applications in chemical, biological and environmental fields and many advantages over other methods (e.g., fluorescence) including, but not limited to, applicability of both fluorophores and chromophores, better detection sensitivity, better monitoring of small changes in chemical and biological properties (i.e., quadratic signal dependence on concentration), and easier signal collection (virtually 100% collection efficiency).

The present techniques may be applied in the a wide range of applications, including but not limited to application of laser wave-mixing spectroscopy for thin-film sensors, fiber optics, laboratory-on-a-chip, capillary cells, sensitive detection of biomolecules with or without labels and tags, sensitive detection of analytes in picomolar, femtomolar and lower concentration levels, sensitive detection of analytes at nano-liter and picoliter-level probe volumes and spatial resolutions (the overlapping volume for the input beams is very small), and sensitive detection of both chromophores and fluorophores. The laser wave-mixing spectroscopy may also be applicable to fluorescing, weakly fluorescing and non-fluorescing samples, and hence, can be used to produce excellent fluorescence-like detection limits for samples that do not fluoresce.

In addition, the present laser wave mixing techniques may be implemented in multi-photon laser wave-mixing optical arrangements based on 3-beam, one-laser, simple optical configurations for gas-phase samples; multi-photon laser wave-mixing optical arrangements based on 2-beam, one-laser, simple optical configurations for liquid-phase samples; and template-based optical alignment for the use of two specially designed templates to provide effective and reliable forward-scattering optical alignments.

With proper designs of the optical configurations for the laser wave mixing, the laser wave mixing may be easily interfaced with to, among others, various continuously flowing liquid-phase chemical instruments and gas-phase chemical instruments. Some examples for the continuously flowing liquid-phase chemical instruments include high performance liquid chromatographs, high performance/power capillary electrophoresis systems, flow injection analysis systems and other similar chemical separation and analytical techniques. Some examples for gas-phase chemical instruments include mass spectrometers, gas chromatograph-mass spectrometers (GC-MS), liquid chromatograph-mass spectrometers (LC-MS), inductively coupled plasma-mass spectrometers (ICP-MS), and other similar analytical methods.

Unique features of the present laser wave mixing methods allow for the effective use of lasers as compared to the conventional light bulbs currently used in commercially available analytical instruments. Detection sensitivity levels may reach orders of magnitude better than currently available models (1,000 to 1,000,000 times, depending on chemical properties, experimental parameters, and optoelectronics).

The following sections describe several implementation examples to illustrate the features and advantages of the laser wave mixing in combination with microarray chips.

Example 1

Imaging of DNA Microarrays by Laser Wave Mixing

Two-dimensional imaging of a DNA microarray may be accomplished rapidly using laser wave mixing with the use of an argon ion laser operating at 515 nm. Intra-spot spatial resolution is obtained with high reproducibility. Imaging of a single row of 10 spots is also performed with high reproducibility. Laser wave-mixing signal is confirmed by monitoring a nonlinear dependence of signal on laser power (i.e., a slope of 2.85 is measured as compared to the expected theoretical slope of 3). The lowest concentration of probe detected that is hybridized with the DNA-microarray is 1 femto molar (fM) (i.e., 0.8 attogram per microliter or 0.1 molecule per square micrometer). Research is in progress and more work is under way to further improve these detection sensitivity levels.

Processing procedure (routine steps previously reported) may be implemented as follows. Suitable DNA microarrays such those marketed by TeleChem may be used. Oligonucleotides are attached to a superamine substrate surface, which contains primary amine groups on a glass slide that carry a positive charge at neutral pH. This charge permits the formation of ionic bonds with the negatively charged phosphate backbone of the DNA. A covalent bond is then formed between the DNA and the surface by ultraviolet light or heat treatment. Chip microarrays are printed with 70-mer oligonucleotides in 200 μm spots and configured as two identical 10×10 sub grids that are spaced 4.5 mm apart. Each microarray chip purchased is further processed to remove unbound target sequences prior to hybridization. The chip is subjected to a 2 minute wash at 25° C. in 2×SSC+0.1% sarkosyl solution. This step creates an ionic atmosphere on the chip so that the printed oligos do not aggregate together. The chip is then washed for 2 minutes in 2×SSC solution. This step removes sarkosyl from the array. Sarkosyl is a detergent that can disrupt future binding reactions. The microarrays are then treated for 2 minutes at 100° C. in D.I. H2O and cooled to room temperature. The boiling water denatures the oligos and helps assure that the oligos are straight for hybridization. Finally, the microarrays are subjected for 2 minutes in icecold 100% ethanol.

Hybridization procedure (routine steps previously reported) may be implemented as follows. Microarray chips are hybridized in a hybridization cassette for approximately 4 hours at room temperature. Hybridization takes place under a 22 mm×22 mm optically flat cover slip with a 5.0 UL probe solution. The probe solution contains 8.0 μL of 1.25× SuperHyb hybridization buffer and 2.0 μL of the universal probe solution. The universal probe solutions contain the complimentary 9-mer oligonucleotide strands. The 9-mer strands have a Cy3 label on the 5' end. The microarrays are then washed for approximately 1 minute in buffer solutions A, B, and C, which contain 2×SSC+0.1% sarkosyl, 2×SSC and 0.5×SSC, respectively. These final washing steps break bonds that are formed from the non-specific matching of the probe. The slides are then whipped dried for 2 minutes before 2-dimensional imaging by laser wave mixing.

Microarrays are probed, excited, scanned and measured by using a novel forward-scattering degenerate four-wave mixing optical setup based on the absorption of the Cy3 label, which has an absorbance maximum near 535 nm. The 514.5 nm line of an argon ion laser is used as the excitation source for the Cy3 label. The resulting signal is sent through a custom designed precision template and detected by a photodiode. During the spatial scanning process, the laser power used is between 2.5 and 5 mW, but not limited to this range. Microarray spots are scanned with the use of a motorized precision actuator in order to achieve automated and reproducible scans. Background optical noise is determined by scanning the blank glass surface between the spots (i.e., the optical blank). No signal is detected on the blank glass surface, assuring that hybridization and washing are performed effectively. Detection sensitivity is excellent and improving continuously. Our preliminary results indicate that laser wave mixing is one of the most sensitive detection techniques for microarray applications. Laser wave mixing also allows intraspot spatial resolution where one can scan, probe and measure bio/chemical contents "within" a single spot on the microarray. Preliminary intra-spot scanning and probing show inhomogeniety within each spot due to inhomogeniety in manufactured preprinted spots. Our laser probe diameter is 25 μm, and hence, it requires much smaller amount of reagents for detection. The microarray chips we purchased come with a marker spot. The marker spots located in the corners of each sub-grid contain Cy3-labeled control oligonucleotides. We can even distinguish variations in signal intensity that are due to differences in sequence composition of the 70-mer oligonucleotide targets.

In this example, the preliminary limit of detection (LOD) so far for the hybridized probe detected is 1 fM (femto molar or 1×10-15 molar). This is better than many published results based on other sensing methods. Reproducible results are also obtained when scanning single-spot profiles repeatedly and when scanning single-row profiles repeatedly. Laser wavemixing signal is also confirmed by monitoring a nonlinear dependence of signal on laser power (i.e., a slope of 2.85 was measured as compared to the expected theoretical slope of 3).

Example 2

Imaging of DNA Microarrays by Laser Wave Mixing

This section describes another example for two-dimensional imaging of a DNA microarray.

A DNA microarray consisting of 200 70-mers oligonucleotide targets was hybridized with a probe solution containing Cy3-labeled random 9-mers at concentrations ranging from 10 micromolar to 1 fentomolar. After hybridization, the DNA microarray was scanned via an argon ion laser operating at 515 nm in a wave-mixing setup. With a laser focused beam diameter of 32 micrometer, intra-spot resolution was obtained. The array was moved via a motorized actuator, allowing the scanning of single spots and single rows of the array. Reproducibility studies were performed. Backward and forward scans of DNA spot rows and single spots were obtained to determine the accuracy and reproducibility of the signal and the movements. Scans of a marker spot were compared with scans of an oligonucleotide sample spot. The lowest concentration of the probe detected after hybridization with the microarray was 1 femtomolar with an S/N of 25 for the marker spot and 7 for the oligonucleotide spot. At S/N of 2, the limit of detection (LOD) of 2.8e-16 M and 5.4e-16 M were determined for marker and oligonucleotide spots, respectively. The 1 femtomolar LOD translates to 0.005 fluorophores per $\mu m^2$ or between 4 to 5 fluorophores in the probe area. To verify the signal at the 1 fM concentration, a power study was also done and the dependency of the signal with laser power was found to be 2.85 with a correlation coefficient of 0.991, which is close to the theoretical cubic dependence expected for the method.

Microarray Fabrication

The DNA microarray slides used came from a kit obtained from TeleChem International Inc (CheckIt Chips, Sunnyvale, Calif., USA) and used as is. The microarray chip (25 mm×76 mm) is printed with 200 oligonucleotides targets in 200-300 μm spots, and configured as two identical 10×10 subgrids spaced 4.5 mm apart. Each spot is about 430 μm from center to center. The individual oligonucleotide targets consist of 70-mers from human, mouse and *E. coli*, which are printed onto a superamine substrate surface. The superamine surface contains primary amine groups on a glass slide that carry a positive charge at neutral pH. This charge permits the formation of ionic bonds with the negatively charged phosphate backbone of the DNA. A covalent bond is formed between the DNA and surface by the treatment with ultraviolet light or heat. There are marker spots placed on each grid whose location is known to determine if the procedure has worked.

Hybridization

The hybridization protocols outlined for use with the kit from Telechem International Inc. were followed with some minor modifications. Each microarray chip is processed to remove the unbound target sequences prior to hybridization. The chip is subjected to a 2 min. wash at room temperature in 2× Saline Sodium Citrate (SSC) Buffer and 0.1% sarkosyl solution. The chip is then washed for 2 min. in 2×SSC solution. The SSC buffer was made from sodium citrate (Fisher Scientific), sodium chloride (VWR) and in-house double distilled water. The 0.1% sarkosyl (sodium lauroyl sarcosinate)

solution was made from molecular biology grade sarkosyl (Fisher Scientific). The microarrays are then treated for 2 min. at 100° C. in distilled water and cooled to room temperature. Finally, the microarrays are subjected for 2 min. in ice-cold 100% ethanol and dried by slightly shaking. A 10 µL drop of probe solution is added to the microarray and a cover slip is gently placed on top to distribute the solution on the entire grid. Microarray chips are hybridized in a hybridization chamber for approximately 3 hours at room temperature. The hybridization chamber consisted of an empty pipette tip container with a damp paper towel at the bottom to prevent the microarray from drying out during the incubation. After the hybridization, washing of the microarray was performed with the SSC buffers and drying by gently shaking was also done.

Probe Solution Dilutions

The probe solution consists of a universal random 9-mer labeled with Cy3 label on the 5' end which will hybridize to all of the spots in the microarray. The probe solutions were diluted to the desired concentration by the following serial dilution scheme developed in conjunction with the manufacturer. In house double distilled deionized water was used when necessary.

All solutions were performed fresh each day and starting from the probe stock solution included in the kit. The pipette used for the serial dilutions was a 2 µL P-2 Pipetman from Rainin Instruments and it has an accuracy of 1.5%+/−0.03 µL.

After hybridization, the microarrays are washed and then dried and are ready for scanning. Buffer background noise was determined by hybridizing a microarray slide with only buffer and no probe solution. No signal was detected on the glass surface between spots assuring that no hybridization occurred in the glass.

Wave-Mixing Setup

Microarrays are scanned in a forward wave-mixing setup and detected by the absorption of the Cy3 label in the array spots that hybridized. The Cy3 label has an absorbance maximum near 535 nm. An argon ion laser (Coherent Innova 90) was used to excite the Cy3 at 515 nm. The argon laser beam is split by a 70:30 beam splitter and later focused by a 10 cm focusing lens to the microarray. As the two pump beams get focused on the DNA microarray spot an interference grating is formed. From this grating, a photon from the probe beam is diffracted creating a signal beam. The signal is then sent through a spatial template and detected by a photo diode detector (ThorLabs, Inc., PDA55, Newton, N.J., USA). A chopper (Stanford Research Systems, Model SR541, Sunnyvale, Calif., USA) connected to a chopper controller (Stanford Research Systems, Model SR540, Sunnyvale, Calif., USA) is used on the weaker pump beam. The reference signal from the chopper is sent to a lock-in amplifier (Stanford Research Systems, Model SR810 DSP, Sunnyvale, Calif., USA) which was then sent to a desktop computer for collection and analysis. During the scanning process, the laser power ranged from 2 to 4 mW. The microarray was mechanically moved by the use of a motorized actuator (Zaber Technologies, ZLA-28, Vancouver, BC, Canada) controlled via a computer through a Basic program. Glass background noise was determined by scanning the glass surface between the spots. Buffer background noise was determined by scanning the buffer slide and comparing to a probe hybridized slide.

Our focused beam diameter is 32 µm and the period in our grating is 13 µm resulting with approximate 2 to 3 grating periods in our probe volume. This formula is an approximation, but it can be useful when trying to get an idea of the approximate number of grating periods present.

Resolution Studies

Our laser spot size was 32 µm at the focal point. This dimension is smaller than the DNA microarray spot of 200-300 µm. The smaller laser spot size allowed us to scan within each spot, and hence, enabling intra-spot resolution. Two different kinds of spots were scanned and their results compared. The first intra-spot scan was of spot 1, which consists of a marker spot. For control purposes, microarray chips have "marker" spots located in the corners of each subgrid. The marker spots contain prelabeled Cy3 single stranded control oligonucleotides. The other type of spot scanned was spot 109, which is a regular oligonucleotide spot. Spots should ideally have a Gaussian distribution of the Cy3 label. This would allow easier quantification of the signal and less background errors. Instead of the spot having one peak, it has two peaks. This could be the result of the printing process of the target oligonucleotides or the uneven hybridization of the probe. The sample spot does have one maximum peak, but it is not centered. Comparison of forward and backward scans within the same spot was done at 20 µm steps. This was done to determine the accuracy of movement of the actuator used. There can be a small discrepancy between the maximum of the two peaks. This can be attributed to the uncertainty of movement of the actuator, which is related to mechanical parameters and can be seen in the specifications that come with the actuator. Each spot was scanned several times in the same direction to determine the reproducibility of the actuator in the same direction. The points have some variation in them that can also results from the actuator uncertainty in movement. Our method of scanning proves to be more reproducible when the scans are compared in the same direction than when compared from different directions.

The resolution chosen to scan the microarray spots was 20 µm. This was done as a middle number since the spot diameter was more closely experimentally calculated to be 200 µm and we wanted to have about 10 scans per spot to keep the time of scanning short and to have enough scans to determine reproducibility. The actuator was capable of the much smaller resolution of 0.1 µm, so it was not a limiting factor. By using 20 µm as the incremental steps for the intra-spot resolution studies, there was some overlap between the fragments scanned. This did not present itself as a problem since the scans were only done to determine reproducibility within different scans performed on the same fragments. By using a shorter focusing lens, the laser spot size could be smaller, and thus, the resolution could be improved.

Commercial scanners take an average or blend of incremental signals to obtain spot profiles. This is needed to obtain clear strong and defined spot signals. As resolution approaches the spot diameter, the spots appear grainy and pixilated, and quantification of the microarray data is impaired. Our method does not suffer from this problem. The signal from the spots is strong when compared to the background and no multi-scanning of the same spot is really needed. Also, the laser beams are focused to a small size diameter which enables the analysis of smaller spots. This would save money in that fewer reagents would be needed, and higher density arrays could be created with smaller spot sizes. Since the amount of DNA to spot or the amount of probe available is often restricted, smaller spots are needed to get a more accurate DNA microarray analysis results. Methods that produce sensitive results with these smaller spots are also needed.

Reproducibility Studies

We performed rapid automated scans of a row of tens spots to demonstrate the use of our method in a more realistic automated way. The increments programmed to the actuator were 350 µm. Data is normalized against the maximum signal of spot 100, which is a "marker" spot. The "marker" spot gives off the highest signal intensity. Spots 10-90 have differences in sequence composition of the 70-mer oligonucleotide targets varying signal intensity compared to the marker spot. This experiment was scanned six times demonstrating mechanical and optical reproducibility.

Sensitivity Studies

To determine the sensitivity of our method, hybridizations with different concentrations of probe solutions were done. The concentration of the probe solutions used to hybridize the microarray ranged from 1 fM (femtomolar) to 10 µM. For comparison purposes, signal detection was done on a marker spot, in this case spot 100, and on a regular spot, spot 190. Spot 100 was hybridized with 1 fM probe solution. To determine the background signal from the microarray that is independent of the probe solution, a microarray slide hybridized with just buffer was detected. This 'buffer slide' was used to quantify the background of spot 100 and spot 190 for the LOD studies.

Spot 100 on the "buffer" slide and spot 100 on the 1 fM slide were analyzed and signal was recorded three times by manually blocking the probe/pump beam. Recording signal three times shows reproducibility in the wave-mixing technique. Laser power was 2 mW. The slide with 1 fM probe solution showed drastically higher signal intensity compared to signal of the buffer slide. The S/N was calculated to be 25. This translated into a detection limit (S/N 2) of 2.8e-16 M for the probe solution.

Regular Spot

Spot 190 was compared with signal of the same spot on another slide hybridized with no probe solution and compared to signal obtained from the glass surface between spots 190-200. A detection limit (S/N 2) of 5.4e-16 M is determined. Laser power used was 2 mW. The marker spot 100 gave peaks with higher signal intensity than spot 190, as expected.

Effective Hybridized Spot

When working with the fM probe hybridized array, it was thought that not all of the microarray spot was actually hybridized since the probe available is so minute. Studies were performed to map the actual area that is hybridized on the array. It was found that there is an effective area of where the probe solution binds to the target molecules. Through mapping of the signal generated, it was found that the effective hybridized area had a diameter of about 84 µm. This number was calculated from the averages of three spot profiles. Spot 109, 1 and 160 were mapped alongside the X-direction using the motorized actuator. It was found that the probe did not bind evenly over the entire spot area. The probe would bind in selected areas effectively reducing the hybridized spot area.

To our knowledge, having 0.005 fluorophores per µm$^2$ or between 4 to 5 fluorophores present in the probe area is the smallest detection limit reported so far for this type of application. For this calculation, it is assumed that the binding ratio between the probe and the target is one to one. We know that there is one Cy3 per 9-mer probe strand, since the synthesis dictated this. According to correspondence with the manufacturer of the chips, the typical DNA hybridization is one to one, but since the probe is a very short chain it is possible that it could hybridize in a higher ratio than the one to one expected, therefore, the ratio could be one to two or even higher; although the higher probability goes with the lower ratios since the concentration of probe (1 fM) is very low.

Wave-Mixing Signal Verification

To make sure the signal obtained from the microarray was real wave-mixing signal, a power dependency study was done. A power plot (wave-mixing signal vs. laser power) was collected from the 1 fM probe solution hybridized array, which is the lowest one hybridized and the microarray that gives our LOD. A fitted 2.85 dependence on laser power was achieved. The R$^2$ value was calculated to be 0.991. The 2.85 result is very close to the theoretical value of three expected. This study confirms that our wave-mixing signal is real.

Laser wave-mixing offers many advantages as an ultra sensitive detection method for microarrays. Excellent sensitivity is achieved by our cubic dependence on laser power and quadratic dependence on signal concentration. This method of detection offers many desirable features including higher sensitivity compared to conventional optical detection methods. To our knowledge, wave-mixing detection of DNA microarrays is the most sensitive detection technique for microarray analysis to date. Other advantages of wave-mixing detection include excellent optical signal collection efficiency because signal is collected against a dark background and the signal is in the form of a coherent laser beam. The small diameter of our laser spot allows for detection of smaller DNA microarray spots which would allow the analysis of higher density array with smaller spot sizes. This will allow the use of fewer reagents and less analysis time. Another advantage of this method is the capability of detecting not just fluorophores, but chromophores as well. This opens the door to more molecules for labeling than the ones currently used, which may have better properties useful in microarray analysis.

Example 3

Separation and Detection of Ni and Cu by Microchip-Based Capillary Electrophoresis Using Laser Wave Mixing Laser wave mixing, an unusually sensitive optical absorption based method, may be used to detect Cu and Ni (the technique is not limited to these metals) after they are separated by a capillary electrophoresis (CE) system embedded on a microchip. The metal ions are chelated with 4-(2-Pyridylazo) resorcinol (PAR) prior to separation. Wavelength shift by PAR allows optical detection using the 514.5 nm line of an argon ion laser. The lowest concentration detected are 0.26 parts-per-billion and 16 parts-per-billion for Ni and Cu, respectively. This corresponds to excellent preliminary detection limits (S/N=2) of 75 parts-per-trillion and 864 arts-per-trillion for Ni and Cu, respectively, using this compact microchip-based chemical separation/analysis system.

A forward-scattering degenerate four-wave mixing optical setup is interfaced to a microchip with built-in microchannels for capillary electrophoresis separation and detection. The 514.5 nm line of an argon ion laser is used as the excitation source with a laser power of 50 mW. A photodiode is used to monitor the signal beam resulting from the microchannel on the chip. Four platinum wires inserted in the access holes of the microchip serve as electrodes for the capillary electrophoresis system. The CE-microchip, obtained from Micralyne, Inc. (Alberta, Canada) is made of Borofloat glass. The microchip substrate is 95 mm long, 16 mm wide and 2.2 mm thick. The microchip (Twin T type) consists of an offset microchannel cross with 8 mm long side arms for sample injection, and an 85 mm long separation and detection channel. The channels are 50 µm wide and 20 µm deep. A 30 kV power supply (Model PS/MJ30P0400-11, Glassman, New Jersey) is used to power the microchip-based CE system via platinum electrodes. The PAR agent is used to chelate the metal ions with +2 charge at a concentration of 1×10-3 M in a 10 mM ammonium phosphate buffer at pH 7.5. The metal ion stock solution is obtained from Fisher. A Millipore water system provides the water for sample preparation and sample solutions are filtered with a 0.22 μm syringe filter. The final low-concentration metal solutions for detection sensitivity studies are obtained by serial dilution from a stock solution.

The PAR buffer solution is filtered before injection into the microchip. A series of low-concentration metal sample solutions are prepared by serial dilutions. The microchip is first conditioned with the PAR-buffer solution and a baseline laser wave-mixing signal is obtained based on the slight optical absorption at 514 nm. Once the wave-mixing alignment is optimized based on this baseline signal, a metal sample solution prepared in the same PAR-buffer solution is injected using an 8 kV injection voltage. The power supply is then switched from the injection mode to the separation mode, using an 8 kV separation power. The PAR-metal complexes are separated as they travel down the separation channel on the microchip since the pKa of the p-phenolic group of PAR is influenced differently by the central metal ion. Copper elutes first after 20 s. and then Ni at 80 s. Hence, chemical separation of this metal pair is very effective with total resolution. Other metals can be separated with excellent resolution using similar parameters, or if necessary, CE voltage levels can be adjusted conveniently to enhance separation resolution. Rinsing and conditioning of the microchip are done using a syringe pump connected to the microchip via a plastic tubing. The plastic tubing is interfaced to the microchip at the microchip access hole via a pipette tip. Rinsing and conditioning are performed before each sample run to flush out any residue and to avoid any contamination. The capillary electrophoresis system used in this setup is a home-built custom-designed system with manual electrode switching between the injection mode and the separation mode with the high-voltage power turned off.

For detection sensitivity studies, a 0.26 parts-per-billion (ppb) Ni sample solution is injected using a 57 s. injection time and a 8 kV injection voltage. This particular design of the microchip does not allow a wide range of sample size injected. One must allow sufficient injection time in order to assure that the sample plug is injected into the side-arm injection microchannel. The injection time (about 50 s.) for this microchip-based capillary electrophoresis system is slightly longer than that for a conventional column-based capillary electrophoresis system. The sample mixture is separated under 8 kV of capillary electrophoresis separation power and detected by laser wave mixing 85 seconds later. A preliminary detection limit (S/N=2) of 75 parts-per-trillion (ppt) is determined for Ni using this microchip-based laser wave-mixing system. For Cu detection sensitivity studies, a 16 ppb Cu sample solution is injected using a 70-second injection time. The Cu peak is detected 53 seconds later using an 8 kV separation power. A preliminary detection limit (S/N=2) of 864 parts-per-trillion (ppt) is determined for Cu. Since Ni has a higher absorption at 515 nm as compared to Cu, Ni yields better laser wave-mixing detection sensitivity.

In the present example, the metal ions were chelated with the chromophore 4-(2-Pyridylazo)resorcinol (PAR) prior to separation which shifted the chromophore's absorption maximum from about 400 nm to about 500 nm. This shift was detected with an argon ion laser operating at 515 nm. The run buffer consisted of 10 mM ammonium phosphate at pH 7.5 with PAR at 1e-3 M concentration. The separation of the two ions was achieved in about 80 s. The Cu ion came out at about 20 s and the Ni ion came out 60 s later. The laser power used in the runs was 50 mW. The injection and separation voltage was 8 kV. Detection limit studies were also performed and the injected LOD for Ni and Cu were 0.26 ppb and 16 ppb, respectively. The detection limits (S/N 2) of 75 ppt for Ni and 864 ppt for Cu were determined. This corresponds to concentration detection limits of 1.3e-9 M for Ni and 1.4e-8 M for Cu. The calculated probe volume for this method was 19 pL. Based on the probe volume used, mass detection limits of 25 zeptomole and 266 zeptomole were determined for Ni and Cu, respectively.

The following provides additional information about this separation techniques.

Microchip

The CE-microchip was obtained from Micralyne Inc. (MC-BF4-TT100, Edmonton, Alberta, Canada). The chip was made from Borofloat glass. The dimensions of the chip substrate were 95 mm by 16 mm by 2.2 mm, with channel plate and cover plate thickness of 1.1 mm each. The chip was of the Twin T type channel which consists of a 100 μm offset cross channel, an 8 mm injection channel and an 85 mm separation channel. The cross-section of the channel was 50 μm in diameter by 20 μm in depth. The chip was conditioned with PAR (1e-3M) buffer before each CE run and cleaned with methanol and then Millipore water at the end of the runs. Conditioning was possible by using a syringe pump (A-99EM, Razel Scientific Instruments, Inc., Stamford, Conn., USA).

High-Voltage Capillary Electrophoresis System

A Glassman high voltage power supply was used (PS/MJ30P0400-11 30 kV, Glassman High Voltage Co., High Bridge, N.J., USA). The electrodes consisted of 4 platinum wires that were inserted in the 4 access holes of the chip reservoirs. The reservoirs consisted of pipette tips cut to fit into the chip access holes. Once inserted, the electrodes were not moved from the reservoirs. Alligator clips connected to the power supply were manually switched from the injection electrodes (sample reservoir and sample waste reservoir) to the separation electrodes (buffer reservoir and buffer waste reservoir). Voltage was turned off while the switching took place. Method of injection used was floating load. Voltage and current were monitored via two voltmeters. The current was kept below 30 μA since at higher values than this Joule heating can impair resolution. Separation and injection voltage for all runs was 8 kV. Injection on the chip was performed from A to B and separation was performed from C to D.

Wave-Mixing Setup

An argon ion laser (Innova 90, Coherent Inc, Santa Clara, Calif., USA) operating at 515 nm was used with a laser power of about 50 mW. A forward wave-mixing setup was used. The argon ion laser beam was split via a 70:30 beam splitter and focused on the sample flowing through the CE-microchip channel through a 10 cm focusing lens. The signal was collected and directed to a PDA55 photodiode (ThorLabs, Inc., Newton, N.J., USA). A chopper (Stanford Research Systems, Model SR541, Sunnyvale, Calif., USA) operating at 200 Hz was used for background noise reduction. The reference signal from the chopper was sent to a lock-in amplifier (Stanford Research Systems, Model SR810 DSP, Sunnyvale, Calif., USA) which was connected to a desktop computer for collection and analysis.

Solutions

PAR [4-(2-Pyridylazo) resorcinol, monosodium salt hydrate] obtained from Aldrich (St. Louis, Mo., USA). PAR was used at a 1e-3 M concentration in a 10 mM ammonium phosphate buffer at pH 7.5, made from ammonium phosphate dibasic (A-1167) and ammonium phosphate monobasic (A-1292) obtained from Sigma (St. Louis, Mo., USA). After the PAR buffer was made it was filtered with a 0.22 um MCE filter obtained from Fisher Scientific (09-719A Fisherbrand, Tustin Calif., USA). The metal ion solutions were made by serial dilution from a 1000 ppm Nickel (SN70-100) and Copper (SC194-100) reference solutions obtained from Fisher Scientific. Water used to make the dilutions has 18 MOhm resistivity (Millipore). The appropriate metal solutions were mixed with the PAR buffer and then solutions were sonicated for about 5 minutes before being introduced into the chip for analysis.

The metal has a +2 charge that will bind with the oxygen of one of the hydroxyl groups of the PAR molecule. Free PAR has an absorption maximum at around 400 nm. When PAR binds to the metal, the absorption maximum at 400 nm decreases, and one gets another peak at around 500 nm. The extinction coefficients for PAR-Cu and PAR-Ni complexes are around 30,000 and 50,000 (1/Mcm). The new peak at around 500 nm was monitored with an argon ion laser operating at 515 nm.

Electroosmosis is a prominent mechanism for controlling fluid flow in microchannels, requiring surface charges. The surface charge on the channel walls causes a diffuse layer of counter ions (1 nm-1 μm thick) to form. When an electric field is applied across a capillary tube containing a buffer solution, electroosmotic flow occurs, in which the solvent migrates toward the cathode or anode. During the experimental runs, the electroosmotic flow was going from the anode to the cathode. This was in the same flow direction as the PAR-metal complexes.

The type of injection used for this work was floating or gated injection. The sample is injected by connecting the positive electrode to the sample reservoir and the negative or ground electrode to the sample waste reservoir. The buffer and buffer waste reservoirs have no field applied. After injection, a field is applied from the buffer reservoir, which now becomes the positive electrode, to the buffer waste reservoir, which mow becomes the negative or ground electrode.

Before each CE run, the channels of the chips were prefilled with PAR buffer at the same concentration that the PAR-metal complexes were made. This prevented the appearance of a PAR peak in the separation since there was no change in PAR concentrations during the run. Wave mixing signal with the PAR solution was obtained and optimized. This was possible since the PAR mixture had a slight absorption at 515 nm, which was detectable with our setup. Once the alignment was optimized, injection of a small amount of metal prepared in the same PAR-Buffer solution was done, followed by separation, all using 8 kV.

Rinsing and conditioning of the microchip were done using a syringe pump connected to the chip via plastic tubing with an attached pipette tip at one end which was placed inside the chip access hole. This operation was performed before the runs were performed and in between them to make sure that no contaminants would interfere. The CE-system used was homemade and the wires had to be changed manually from the injection position to the separation position. This manual change had to be done with the power off for safety reasons.

Injection of a mixture of Cu and Ni at a concentration of 2 ppm was first done. Copper and Nickel PAR complexes were made and then mixed and put in the sample reservoir by a disposable syringe. All of the other reservoirs were filled with PAR buffer solution at the same concentration as the one already in the microchannels. A platinum electrode was inserted into each of the reservoirs. Cu came out first during the separation at approximately 20 s. and then followed by Ni at approximately 80 s.

Due to the design of the chip, one gets about the same size of sample plug injected, regardless of the injection time, as long as enough time is provided to get to the separation channel.

Studies were performed to determine the lowest concentration of solution injected in the reservoirs that could be detected by this method. The lowest concentration of Ni solution detected was 0.26 ppb. The injection time was 57 s and the Ni peak came out at around 85 s. The LOD (S/N 2) calculated was 75 ppt. The Cu concentration injected was 16 ppb, with an injection time of 70 s. The peak came out at 53 S. This gave a LOD of 0.9 ppb Cu. Ni has a higher absorption at 515 nm than Cu, and thus, it gave a better LOD at this wavelength. These results were compared to current methods for metal detection performed in microchips, and to the best of our knowledge, our results show greater sensitivity than any other method.

The probe volume of the chip was 19 pL. This was calculated based on our focused laser beam diameter of 35 μm. This probe volume yields a mass LOD of 25 zeptomole for Ni and 266 zeptomole for Cu. The small diameter of the laser spot allows the use of smaller chip channels for analysis. The spot can be even made smaller with a smaller focal length lens in the setup.

To enhance limits of detection (LOD), direct loading can be utilized to enhance the size of the sample plug. To reduce sample and reagent consumption, smaller microchannels can be used. Also, to reduce background, lower concentrations of PAR buffer should be used or none at all, provided the metal ions still remain chelated by PAR.

Laser wave-mixing offers many advantages as a very sensitive detection method for CE-microchips. Excellent sensitivity is achieved by our cubic dependence on laser power and quadratic dependence on signal concentration. Other advantages of wave mixing detection include excellent optical signal collection efficiency because signal is collected against a dark background and the signal is in the form of a coherent laser beam.

The small diameter of our laser spot allows for easy coupling of wave mixing to even smaller microchip channels. This will allow the use of fewer reagents, fewer waste, and faster separations.

Another advantage of this method is the capability of detecting not just fluorophores, but chromophores as well. This opens the door to more molecules for labeling than the ones currently used, which may have better properties useful in microchip analysis. Newer methods of detection are needed that do not rely on fluorescence properties of the analytes for detection. Absorption-based wave mixing is a more universal detection technique applicable for CE-microchip analysis which would allow broader applications than fluorescence.

Example 4

Ultrasensitive Detection of Proteins and Antibodies by Laser Wave Mixing Using a Chromophore Label Laser wave mixing is presented as a sensitive optical method for the detection of proteins bound to Coomassie Brilliant Blue (CBB), a chromophore label, using a simple low-power He—Ne laser. Proteins are mixed with the CBB label and incubated at room temperature for 15 minutes. After incubation, analytes are flowed through a 350 μm i.d. capillary cell and analyzed using nonlinear wave-mixing optical detection. Signal can be detected after only a few minutes of incubation time and maximum signal is obtained after 10 minutes of room temperature incubation. Different ratios of CBB to protein are used and studied. The best concentration ratios and incubation times vary depending on the type of molecule bound to CBB. Each case is studied separately and the optimum conditions are determined. A preliminary detection limit of $4.7 \times 10^{-19}$ M (i.e., $2.4 \times 10^{-22}$ mol or $3.2 \times 10^{-17}$ g/mL) is determined for BSA. A preliminary detection limit of $9.3 \times 10^{-14}$ M (i.e., $3.7 \times 10^{-17}$ mol or $1.4 \times 10^{-11}$ g/mL) is determined for HPV antibody. All solutions were prepared in aqueous buffer without the addition of organic modifiers.

Solutions

Coomassie Brilliant Blue (CBB) dye reagent was prepared according to instructions from Bio-Rad Laboratories (Hercules, Calif., USA) and used for determining concentration of solubilized protein. A pH 4 Tris HCl buffer solution (0.50 M) was prepared in deionized double distilled water filtered with a Whatman 44 ashless filter. Protein standards of Ovalbumin and Bovine Serum Albumin (BSA) were obtained from Sigma Chemical (St. Louis, Mo.). Human Papillomavirus antibody (HPV) was used as received from US Biological (Swampscott, Mass., USA). All protein stock solutions were prepared by dissolving a weighed amount of protein in pH 4 Tris HCl buffer solutions. The stock protein solution was then serially diluted down to working concentrations. All solutions were made fresh each day.

For the time studies, a specific amount of CBB dye reagent was pipetted into a 2 mL plastic vial containing the protein solution, mixed with a vortexer and incubated at room temperature before each measurement. Samples were then pumped into a capillary detector cell and were flowed via a peristaltic pump.

Wave-Mixing Signal Measurement

A forward-scattering degenerate four-wave mixing set up was used for the protein assay measurements. A He—Ne laser (Uniphase, Manteca, Calif., USA; Model 1125P) operating at 632.8 nm was used as the excitation light source. The output of the laser beam is split by a 70/30 beam splitter which formed two input excitation beams. The reflected beam from the beam splitter has the higher laser intensity, and therefore, it is used as the forward pump and probe beam. The transmitted beam is used only as the pump beam. A mechanical chopper is used to modulate the amplitude of the pump beam at 200 Hz. The chopper control was interfaced to a lock-in amplifier (Stanford Research Systems, Model SR810 DSP, Sunnyvale, Calif., USA), which was interfaced to a computer for data acquisition and display. Together these two input excitation beams travel equal distances before they are focused at the capillary detector cell creating a small laser probe volume. Two signal beams are generated and they propagate in the forward direction. These signal beams resemble the two input excitation beams. One signal beam is detected using a photodetector (ThorLabs, Inc., Model PD55, Newton, N.J., USA) after passing through an iris and a focusing lens.

The wave-mixing detector cell is a 350 ▢m inner-diameter capillary cell (Polymicro Technologies Inc., Phoenix, Ariz., USA) interfaced to a peristaltic pump (Rainin, Woburn, Mass., USA) to keep the analyte solution flowing at a speed of 2.5 mL/min. Once the excitation beams are aligned, they counter propagate through the detector cell. The probe beam intersects the pump beam inside the cell at a very small angle. The wave-mixing signal may be maximized by adjusting the alignment to optimize the signal. An alignment dye solution, Nile blue (Aldrich, Milwaukee, Wis., USA), is first injected into the system to generate the wave-mixing signal, which is visible to the naked eye, and the setup optimized. This visible signal beam is then conveniently directed to the photodetector. The optical alignment remains stable all during the experimental run. To verify this, the alignment dye is reintroduced to the system after all the protein solutions are analyzed.

In acidic environments, the CBB dye molecule exists as the unprotonated anionic dye species. The CBB protein-binding dye may also exist in the cationic and the neutral form, although it is the anionic form of CBB that complexes with the protein of choice. Modifications of the conjugated system produce the neutral and cationic form of the dye, which changes the dye species absorbance maximum. The dye binds to the tertiary amine functional group of the protein causing the shift in the absorption spectrum. The CBB dye does not bind to small molecular weight molecules so little interference should be expected.

For the CBB with protein solution, the protein used was BSA at a concentration of 2.4e-7 M in Tris-HCl buffer. For the solution of CBB with no protein, only Tris-HCl buffer was added. The solutions were incubated 20 minutes before being read in the UV-Vis spectrophotometer. A shift in the absorption maximum of the dye from approximately 490 nm to 600 nm is observed due to the binding of the protein to the anionic dye. The magnitude of the absorption maximum shift at higher wavelengths is a function of the protein concentration. This protein-caused shift can be monitored at more than the traditional 595 nm wavelength that the Bradford assay dictates. The more protein is available to bind to the CBB, the higher the shift to higher wavelengths. The 633 nm wavelength is also a good wavelength to monitor in addition to the 595 nm line. This allows one to use a compact inexpensive He—Ne 633 nm laser to monitor the amount of protein present in the wave-mixing studies.

The ratio of dye to protein plays an important role in the binding and the reaction, and consecutively, the detection. Enough protein must be present to bind to the CBB so that an absorption shift can be observed. If too much CBB is present, this increases the background signal, thus can mask the wave mixing signal. An exact amount of CBB must be present so that it binds to all the protein present in solution and it does not create a large background signal. The wave-mixing signal generated from CBB-BSA is collected in three signal intervals using a beam blocker. The beam blocker prevents the signal from passing through the end of the experimental set up and onto the detector. By manual movement of the beam blocker three signal peaks are collected. The wave-mixing signal is compared to a "blank" solution, which consists of pure buffer and CBB dye. Although, the blank solution has zero amount of protein a small background signal was still observed. Minimal absorption can be expected because the CBB dye still has a small absorption peaks in the monitored range without any bound protein. The limit of detection for BSA calculated for S/N 2 was 4.7e-19 M, which corresponds to 3.2 e-17 g/mL or 32 attogram/mL or 2.35e-22 mol (calculated using a 68 KDa M.W. and a 500 µL sample volume). This corresponds to ~142 molecules of protein that are being detected by the wave-mixing method. To our knowledge, this is the best detection limit for protein detection in a similar assay reported to date.

To prove the broader applicability of this method, antibodies were also detected by wave mixing. Human Papillomavirus antibody (HPV) is related to tumor detection in people and has been correlated with each of the progressive stages of cervical cancer. Detecting HPV at a more sensitive level is very important since it will aid in earlier diagnosis of possible cancer presence in patients. The HPV antibody is mixed with CBB at different ratios and incubation times and binding ratios are optimized. The protein complex formed was made from 75 μL of CBB dye and 400 μL of HPV and incubated for 15 minutes. The experiment followed the same guidelines as for CBB-BSA concentration study. The LOD obtained for HPV was 9.3e-14 M (S/N 2). This corresponds to 1.4e-11 g/mL or 3.7e-17 mol (based on 400 μL sample volume).

Incubation time studies were also performed with BSA and HPV. HPV shows a maximum faster than BSA. This is probably due to the larger mass of HPV which can bind more CBB molecules than BSA. If more binding sites are available for CBB, the reaction will be faster. BSA reached a maximum at around 18 minutes, based on the best fit line, and HPV reached it at around 10 minutes. For this time study, 75 μL of CBB were mixed with 400 μL of HPV at a 3.6e-9 M concentration in tris-HCl buffer. The concentration of BSA was maintained at 1.15e-12 M and 800 μL of BSA was mixed with 25 μL of CBB in the same tris-HCl buffer. After the maximum signal is reached, signal starts to decrease. This is probably due to aggregation of the CBB-protein complex occurring which makes the complex precipitate out of solution, decreasing the signal intensity. This study shows how wave mixing can be almost immediately detected. No long incubation times are required for sensitive signal collection. This eliminates total assay time which is more apparently important when multiple assays are required.

A time study for Ovalbumin was also made. This protein behaved similarly as BSA and HPV when bound to CBB and monitored with wave mixing. A ratio of 100 μL CBB to 800 μL Ovalbumin was used. Data was collected similarly as in other studies.

Such low levels of detection for BSA and HPV were possible since wave missing offers many advantages over conventional laser-based methods including excellent optical signal collection efficiency since the signal is in the form of a coherent laser-like beam, square dependence on sample concentration and cubic dependence on laser power. Our detection sensitivity levels and concentration limit of detection are much better than those of many other sensitive methods. Our detection limits compare favorably to those of other methods for protein detection. Our results are a big improvement over results obtained by laser-induced fluorescence (LIF). By performing time studies, we can see that a long incubation time is not needed to obtain sensitive results. We have also cut down on the amount of reagents that are needed to perform protein detection. This is very important when samples are limited due to price or to availability. Another key feature of this study is that the samples were analyzed in pure buffer without the addition of an organic modifier to enhance the wave mixing signal. This is very important since for biological analysis it is very desirable to keep everything at physiological conditions as much as possible.

Laser wave mixing offers many advantages as an ultra sensitive detection method for both fluorescing and non-fluorescing analytes. Analytes may be labeled with chromophores, not just fluorophores. Excellent sensitivity is achieved by our cubic dependence on laser power and quadratic dependence on signal concentration. In our non-linear wave-mixing detection, absorbance is determined based on a large absolute positive signal against a virtually dark background. We have demonstrated that wave mixing as an ultra-sensitive detection of proteins and antibodies. Advantages of wave mixing includes more sensitive detection, more rapid analysis, less amount of reagents used, lower cost and less environmental waste, and hence, wave mixing is an attractive novel method for protein determination.

Only a few implementations are disclosed. However, it is understood that variations and enhancements may be made.

What is claimed is:

1. A method, comprising:
providing a microarray comprising a plurality of DNA cells having DNA samples and a blank area between two adjacent DNA cells that is free of DNA samples, wherein the blank area is separate from the two adjacent DNA cells;
placing the microarray in an optical degenerate four-wave mixing (DFWM) system operating at an optical wavelength within an absorption spectral range of the DNA cells to generate a DFWM signal in one of the DNA cells, wherein the DFWM system includes a laser to produce a laser beam at the optical wavelength, DFWM optical elements to split the laser beam into a plurality of input laser beams that spatially overlap with one another at a beam overlap spot positioned within the one DNA cell in the microarray with desired crossing angles with respect to one another for optical DFWM operation within the one DNA cell in generating the DFWM signal of the one DNA cell, and an optical detector located to receive light of the DFWM signal produced at the beam overlap spot due to the optical DFWM operation;
placing a single template between the microarray and the optical detector comprising holes arranged to selectively transmit the DFWM signal from the microarray to the optical detector and to block pump light and probe light in the DFWM system from entering the optical detector;
measuring an output of the optical detector to represent the DFWM signal of the one DNA cell;
moving the microarray relative to the beam overlap spot out of the one DNA cell to an adjacent blank area between the one DNA cell and a next adjacent DNA cell;
removing a local background noise in the measured DFWM signal of the one DNA cell by using at least a DFWM measurement of the blank area between the one DNA cell and the next adjacent DNA cell; and
scanning a position of the microarray to place other DNA cells of the microarray in the DFWM system to get respective DFWM signals,
wherein using the beam overlap spot within each DNA cell to sample and to detect a minute quantity of a DNA sample, using the template in operating the detector to reduce background noise, the removing of the local background noise in the measured DFWM signal of specific DNA cell by using a DFWM measurement of the blank area between adjacent DNA cells collectively allow for a limit of detection capability at a zeptomole level in the DNA cells.

2. The method of claim 1, further comprising:
using the measured signal in the blank area to determine a level of hybridization and washing in preparing the DNA cells and background optical noise.

3. The method of claim 1, further comprising:
scanning the position of the microarray to place different locations within the one DNA cell in the DFWM system to obtain different DFWM signals from the one DNA cell; and
using the different DFWM signals from the one DNA cell to determine spatial inhomogeniety within the one DNA cell.

4. The method as in claim 1, further comprising using a forward-scattering DFWM configuration in the DFWM system to produce each DFWM signal.

5. The method as in claim 4, wherein the forward scattering DFWM configuration receives one pump beam and one probe beam to produce a DFWM signal.

6. The method as in claim 1, further comprising using a backward-scattering DFWM configuration in the DFWM system to produce each DFWM signal.

7. The method as in claim 1, wherein the scanning is carried out at 20 micron steps.

8. The method as in claim 1, wherein the scanning is carried out by moving the microarray.

9. The method of claim 8, wherein the microarray is moved using a computer-controlled actuator.

10. The method of claim 1, wherein the laser beam has an output power in the range 2 to 4 milli Watts.

11. The method of claim 1, wherein one or more of the plurality of input laser beams is delivered using a fiber optic cable.

12. The method of claim 1, comprising using a computer that is coupled to the optical detector to analyze DFWM signals.

* * * * *

UNITED STATES PATENT AND TRADEMARK OFFICE
CERTIFICATE OF CORRECTION

PATENT NO. : 8,268,551 B2
APPLICATION NO. : 10/540224
DATED : September 18, 2012
INVENTOR(S) : William G. Tong Page 1 of 1

It is certified that error appears in the above-identified patent and that said Letters Patent is hereby corrected as shown below:

In Column 1, Line 40, please delete "ultrasensative" and insert -- ultrasensitive --, therefor.

In Column 1, Line 57-58, please delete "mciroarray" and insert -- microarray --, therefor.

In Column 7, Line 6, please delete "11," and insert -- I1, --, therefor.

In Column 7, Line 7, please delete "12" and insert -- I2 --, therefor.

In Column 7, Line 8, please delete "11:12," and insert -- I1:I2, --, therefor.

In Column 8, Line 66, please delete "2231," and insert -- 223', --, therefor.

In Column 11, Lines 55-56, please delete "inhomogeniety" and insert -- inhomogeneity --, therefor.

In Column 11, Line 56, after "due to", please delete "inhomogeniety" and insert -- inhomogeneity --, therefor.

In Column 12, Line 17, please delete "fentomolar." and insert -- femtomolar. --, therefor.

In Column 16, Lines 49-50, please delete "arts-per-trillion" and insert -- parts-per-trillion --, therefor.

In Column 20, Lines 11-12, please delete "53 S." and insert -- 53 s. --, therefor.

In Column 24, Line 60, in Claim 3, please delete "inhomogeniety" and insert -- inhomogeneity --, therefor.

Signed and Sealed this
Twelfth Day of February, 2013

Teresa Stanek Rea
*Acting Director of the United States Patent and Trademark Office*